(12) United States Patent
Schramm et al.

(10) Patent No.: US 9,522,159 B2
(45) Date of Patent: Dec. 20, 2016

(54) **TREATMENT AND PREVENTION OF *P. AERUGINOSA* INFECTIONS USING COFORMYCIN ANALOGS**

(71) Applicants: Albert Einstein College of Medicine, Inc., Bronx, NY (US); Victoria Link Limited, Wellington (NZ)

(72) Inventors: Vern L. Schramm, New Rochelle, NY (US); Peter Charles Tyler, Wellington (NZ); Richard Fröhlich, Graz (AT)

(73) Assignees: Albert Einstein College of Medicine, Inc., Bronx, NY (US); Victoria Link Limited, Wellington (NZ)

( * ) Notice: Subject to any disclaimer, the term of this patent is extended or adjusted under 35 U.S.C. 154(b) by 0 days.

(21) Appl. No.: 14/426,775

(22) PCT Filed: Sep. 10, 2013

(86) PCT No.: PCT/US2013/058844
§ 371 (c)(1),
(2) Date: Mar. 9, 2015

(87) PCT Pub. No.: WO2014/043046
PCT Pub. Date: Mar. 20, 2014

(65) Prior Publication Data
US 2015/0231165 A1    Aug. 20, 2015

Related U.S. Application Data

(60) Provisional application No. 61/699,496, filed on Sep. 11, 2012.

(51) Int. Cl.
*A61K 31/7056*    (2006.01)
*A61L 31/16*    (2006.01)
*A61L 29/16*    (2006.01)
*C12Q 1/34*    (2006.01)

(52) U.S. Cl.
CPC .......... *A61K 31/7056* (2013.01); *A61L 29/16* (2013.01); *A61L 31/16* (2013.01); *C12Q 1/34* (2013.01); *A61L 2300/406* (2013.01); *G01N 2333/978* (2013.01)

(58) Field of Classification Search
None
See application file for complete search history.

(56) References Cited

U.S. PATENT DOCUMENTS

| 5,872,104 | A | 2/1999 | Vermeulen et al. |
| 8,394,950 | B2 * | 3/2013 | Furneaux ................. C07H 5/10 536/27.1 |
| 2009/0227532 | A1 | 9/2009 | Furneaux et al. |
| 2011/0190265 | A1 | 8/2011 | Schramm |

FOREIGN PATENT DOCUMENTS

WO    WO2007/097643    *    8/2007

OTHER PUBLICATIONS

Yale School of Medicine document—Children's Hospital of Illinois—Pseudomonas aeruginosa Information Sheet—2006.*
Tyler et al., Journal of the American Chemical Society, 2007, 129, pp. 6872-6879.*
PCT International Search Report and Written Opinion, dated Jan. 16, 2014 in connection with PCT International Application No. PCT/US2013/58844, 11 pages.
Guan R et al., entitled "Methylthioinosine Phosphorylase from Pseudomonas aeruginosa. Structure and Annotation of a Novel Enzyme in Quorum Sensing," Biochemistry, Feb. 22, 2011; 50(7): 1247-1254.

* cited by examiner

*Primary Examiner* — Traviss C McIntosh, III
(74) *Attorney, Agent, or Firm* — Amster, Rothstein & Ebenstein LLP

(57) ABSTRACT

Methods and devices are disclosed for treating or preventing infections in a subject due to *Pseudomonas aeruginosa* using coformycin analogs and inhibitors of *Pseudomonas aeruginosa* 5'-methylthioadenosine deaminase (MTADA).

19 Claims, 7 Drawing Sheets

```
PA0134   EHGHVRALDHATYLLPQLPADLPLEEHPQRLLLPGFVDCHVHYPQLG---VIASYGTQLL 116
PA1521   EDGKVARLGDAETLLGEIG-EVEVFEYRDALITPGFIDTHIHFPQTG----MIASYGEQLL 94
PA0142   EDGRIVELLGAGQQPAQPC--ASQFDASRHVVLPGLVNTHHHFYQTLTRAWAPVVNQPLF 84
PA3170   RDGQIALVAPREQAMRHGA--TEIRELPGMLLAPGLVNAHGHSAMSLFR---GLADDLPLM 90
2PLM      ENGTIKRVLQGEVK--------VDLDLSGKLVMPALFNTHTHAPMTLLR--GVAEDLSFE73
PA2499   ------------------------------------------------------------
PA0437   ADGRIAALVPMEQAADDAG---ERLDGAGGLAVPPFIEPHVHLDTTQTAG-QPEWNRSGT 75
PA0148   MYEWLNALPKAELHLHLEG------TLEPELLFALAERNRIALPWNDVETLRKAYAFNNL 54
PA3480   KSDKWIRRMAQEHG----------------MIEPFVERQVR------------------ 28

PA0134   DWLETHTFPAEQRFADAGYAAAQAELFLDELLRHGTTTALVFGTVHAVSAEAFFQAAQ-- 174
PA1521   DWLNTYTFPTERQFGDQAHADQVAEIFLQELLRNGTTTALVFGSVHRQSVESLFEAAR-- 152
PA0142   PWLKT-LYPVWARLT-PEKLELATKVALAELLLSGCTTAADHHYLFPGGLEQAIDVQAGV 142
PA3170   TWLQDHIWPAEGQWVSEDFIRDGTELAIAEQVKGG-ITCFSDMYFYPQAICGVVHDSG-- 147
2PLM      EWLFSKVLPIEDRLT-EKMAYYGTILAQMEMARHG-IAGFVDMYFHEEWIAKAVRDFG--129
PA2499   -------------MSDETFMREAIALARANVEAGG------------RPFGAVLVRDG-- 33
PA0437   LFEGIERWAQRKALLSHEDVKQRAWQTLKWQIANGVQHVRSHVDVSDPTLTALKAMLEVR 135
PA0148   QEFLDLYYAGADVLRTEQDFYDLTWAYLQKCKAQNVVHVEPFFDPQTHTDRGIPFEVVLA 114
PA3480   ------------------GADDSRVISYGVSSYGYDVRCAAEFKVFTNIHSAVVDPKN-- 68

PA0134   ----KRRLRMIAGKVLMDRN----APPALCDTAASGYAESRALIERWHGNG---RLQYAV 223
PA1521   ----RLDLRLIAGKVMMDRN----APDYLTDTAESSYRDSKALIERWHGQG---RLLYAV 201
PA0142   VEELGMRAMLTRGSMSLGEKDGGLPPQQTVQEAETILADSERLIARYHQRGDGARVQIAL 202
PA3170   -----------VRAQVAIPVLD----FPIPGARDSAEAIRQGMALFDDLKHHP---RIRIAF 191
2PLM      ---------MRALLTRGLVD-------SNGDDGGRLEENLKLYNEWNGFEG--RIFVGF170
PA2499   ------------------------------RVLARGVNQIHETHDPS---------- 50
PA0437   G--------EVAPWVDLQIVA-------FPQEGILSYPNGLELLEESLRLG---ADVVGA 177
PA0148   G-----------------------------IRAALRDGEKLLGIRHGLI---------- 134
PA3480   ---------------------------------------FDEKSFVDIN------------ 78

PA0134   TPRFAPTSSP--EQLAAAARLLDEYPGVYLHTHLSENLKEVAWVGELFPQAQDYLDVYHR 281
PA1521   TPRFAPTSTA---EQLDMAARLLREHPGVYLHTHLSENLKEIEWVKELFPERSGYLDVYDH 259
PA0142   APCSPFSVTP--EIMRASAEVAARHD-VRLHTHLAETLDEEDFCLQRFGLRT--VDYLDS 257
PA3170   GPHAPYTVSD--DKLEQILVLTEELD-ASIQMHVHETAFEVEQAMERNGERF--LARLHR 246
2PLM      GPHSPYLCSE--EYLKRVFDTAKSLN-APVTIHLYETCKE----------EYDLEDILN216
PA2499   ------------------------------------------------------------
PA0437   IPHFEFTRELGVESLHKAIDLAKRYD-LPVDVHCDEIDDEQSRFLETLAMLAHRDGLGAR 236
PA0148   -----------------------------------------------------LSFLRH 140
PA3480   ------------------------------------------------------------

PA0134   DLDGLVGNFLPGREADFVALDLAAT------PMIAQRMEHAR-GLADTLFVLNTLGDDRA 441
PA1521   ELDDRIGSFATSNEADFVVLDYHAT------PLLSYRLSQAG-SLAERLFALTILGDDRT 419
PA0142   GRSD-IGELAPGKQADLALFKLDELRFSGSHDPLSALLLCAA-DRADRVMVGGAWRVVDG 425
PA3170   GLERLIGSLEAGKAADLVAFDLSGLAQQPVYDPVSQLIYASGRDCVRHVWVGGRQLLDDG 417
2PLM      GFKS--GKIEEGWNADLVVIDLDLPEMFPVQNIKNHLVHAFS-GEVFATMVAGKWIYFDG382
PA2499   GLYRQWRQRQA-------------------------------------------------- 151
PA0437   GLREY--GIEVGHPANLLVLPARDGFDAVRRQVPVRYSIRGGRLLAETVPAQTTVFLEQA 414
PA0148   VFDDMSQHTILDMLERGVKVTVNSD---------DPAYFGGYVTENFHALQQSLGMTEE 300
PA3480   SYKDRGGKYQGQRGVTLFKA---------------------------------------- 188
```

FIGURE 3

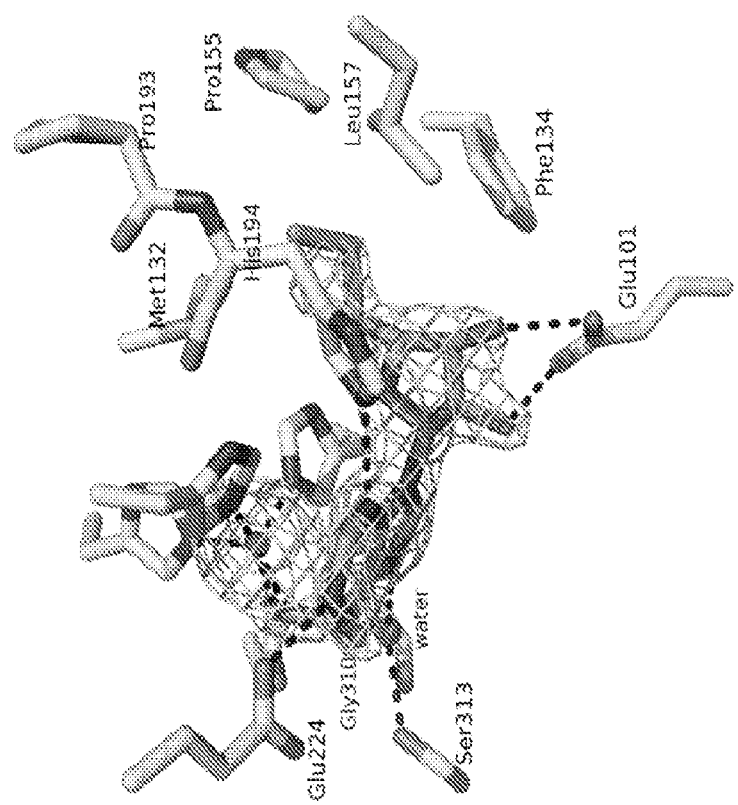
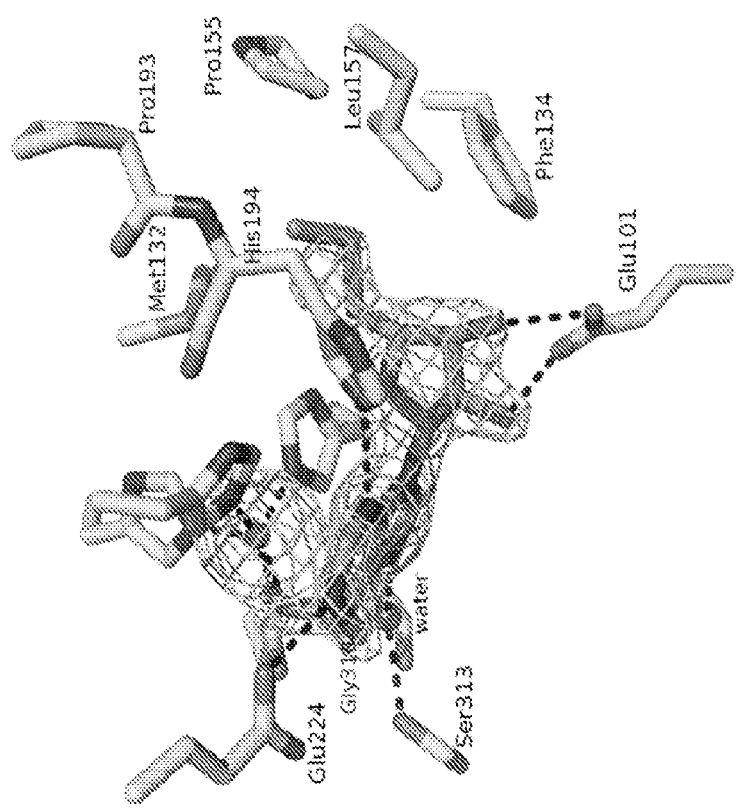
FIGURE 6

TREATMENT AND PREVENTION OF *P. AERUGINOSA* INFECTIONS USING COFORMYCIN ANALOGS

CROSS-REFERENCE TO RELATED APPLICATIONS

This application is a U.S. national stage entry under 35 U.S.C. §371 of PCT International Patent Application No. PCT/US2013/058844, filed on Sep. 10, 2013, which claims the benefit of U.S. Provisional Patent Application No. 61/699,496, filed on Sep. 11, 2012, the contents of all of which are hereby incorporated by reference.

STATEMENT OF GOVERNMENT SUPPORT

This invention was made with government support under grant number GM041916 awarded by the National Institutes of Health. The government has certain rights in the invention.

FIELD OF THE INVENTION

The invention relates to treating and preventing infections due to *P. aeruginosa* using coformycin analogs and inhibitors of *Pseudomonas aeruginosa* 5'-methylthioadenosine deaminase (MTADA).

BACKGROUND OF THE INVENTION

Throughout this application various publications are referred to in parentheses. Full citations for these references may be found at the end of the specification before the claims. The disclosures of these publications are hereby incorporated by reference in their entireties into the subject application to more fully describe the art to which the subject application pertains.

*Pseudomonas aeruginosa* is a Gram-negative bacterium and a major opportunistic human pathogen, accounting for approximately 15% of all hospital infections (1). Immunocompromised patients and patients with comorbid illnesses are especially susceptible to the infection (1, 2). *P. aeruginosa* has multiple antimicrobial resistance mechanisms making infections difficult to treat (3). High morbidity and mortality rates have been reported in *P. aeruginosa* infections, especially for late-onset ventilator associated pneumonia (4, 5). In *P. aeruginosa*, the production of virulence factors and biofilm formation are regulated by quorum sensing (QS) systems (6). QS involves bacterial cell-to-cell communication by small molecules. QS allows bacteria populations to adjust behavior in response to environmental conditions (4). Communication in QS relies on signaling molecules including the N-acyl-homoserine lactones (AHLs) found in *P. aeruginosa* and most other Gram-negative bacteria. AHLs are synthesized as the bacterial cell density increases. When the concentrations of AHLs reach a critical threshold, the signal molecules bind to specific receptors and regulate target genes expression. A major QS system in *P. aeruginosa* includes las and rhl, which use 3-oxo-$C_{12}$-homoserine lactone and $C_4$-homoserine lactone as signaling molecules, respectively. QS signaling is correlated with the virulence of *P. aeruginosa* infections. Deletion of single or multiple QS genes in *P. aeruginosa* reduced virulence in several mouse models (5). The presence of QS signaling molecules and expression of QS-responsive genes in *P. aeruginosa* have been detected in sputum samples of cystic fibrosis patients. And most recently, production of QS-dependent virulence factors of *P. aeruginosa* have been linked to the development of ventilator-associated pneumonia (6). Since inhibition of QS biosynthetic pathways does not affect cell growth, blocking QS synthesis has been proposed as a strategy to attenuate the virulence of bacterial infections without causing drug resistance (7).

AHL synthase catalyzes the production of AHL using S-adenosylmethionine (SAM) and acylated-acyl carrier protein as precursors. The reaction produces 5'-methylthioadenosine (MTA) as a product. MTA is also an important product from polyamine biosynthesis and is recycled by a SAM salvage pathway (8). In most bacteria, MTA is degraded by 5'-methylthioadenosine nucleosidase (MTAN) to adenine and 5-methylthio-α-D-ribose. Inhibition of *E. coli* and *V. cholerae* MTANs with transition state analogue inhibitors or by gene deletion, disrupts quorum sensing, and reduces biofilm formation, supporting MTAN as a target for QS in most Gram negative bacteria (8). Mammals do not express an MTAN, nor do they have QS pathways, giving species specificity to this target.

In eukaryotes and archaea, MTA degradation is catalyzed by 5'-methylthioadenosine phosphorylase (MTAP) which converts MTA and phosphate to adenine and 5-methylthio-α-D-ribose 1-phosphate (9). *P. aeruginosa* was originally thought to be a bacterial anomaly, possessing an MTAP (PA3004 gene) instead of MTAN. The PA3004-encoded protein was recently characterized and found to prefer methylthioinosine (MTI) as substrate (10). It remains the only known example of a specific MTI phosphorylase (MTIP). The discovery of MTIP suggested that MTA must be deaminated in *P. aeruginosa*. MTA catabolism in *P. aeruginosa* was examined using [8-$^{14}$C]MTA. A MTA→MTI→hypoxanthine pathway was established and no significant MTAP or MTAN activity was observed (10). These results established a functional PaMTIP in cells and extracts and implicated the existence of an MTA deaminase (MTADA) to convert MTA to MTI (FIG. 1). If MTADA is directly and solely responsible for MTA degradation in *P. aeruginosa*, inhibition of PaMTADA would be functionally similar to that of MTAN in other bacterial species, causing MTA product inhibition of AHL synthase and disruption of quorum sensing in *P. aeruginosa* (11). This pathway is unprecedented in bacteria, but *Plasmodium* species also possess a similar two-step pathway of MTA degradation. In the case of *Plasmodium* species, both the purine nucleoside phosphorylase and the adenosine deaminase (ADA) are broad-specificity enzymes, capable of functioning as MTIP and MTADA, respectively. However, inosine and adenosine are preferred substrates and MTI and MTA are secondary substrates (12, 13).

Recently, the first specific MTA deaminase has been reported in *Thermotoga martima* (14). The TmMTADA can deaminate MTA, S-adenosylhomocysteine and adenosine but prefers MTA. TmMTADA was identified by using structure-based docking with high-energy forms of potential substrates and the activity validated by enzymatic assays with purified protein. A crystal structure of TmMTADA in complex with S-inosylhomocysteine, the product of SAH deamination, was determined in the same study, revealing the key residues for binding substrates in the active site (14). These findings on TmMTADA guided the search for PaMTADA.

The present invention addresses the need for compounds that attenuate the virulence of infections due to *P. aeruginosa* without causing drug resistance.

SUMMARY OF THE INVENTION

The invention provides methods of treating or preventing a *Pseudomonas aeruginosa* (*P. aeruginosa*) infection in a subject comprising administering to the subject a compound of formula (I) in an amount effective to treat or prevent a *P. aeruginosa* infection in a subject, wherein formula (I) is

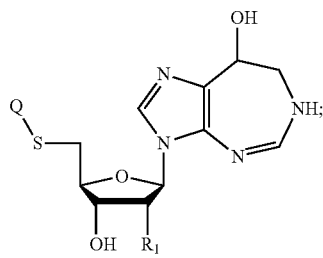

wherein R1 is H or OH; and wherein Q is C1-C6 alkyl, aryl or aralkyl, wherein Q is optionally substituted with one or more methyl, hydroxyl or halogen; or a pharmaceutically acceptable salt thereof or an ester thereof.

The invention also provides compositions for treating or preventing a *Pseudomonas aeruginosa* (*P. aeruginosa*) infection in a subject comprising a compound of formula (I) in an amount effective to treat or prevent a *P. aeruginosa* infection in a subject and a pharmaceutically acceptable carrier.

The invention provides implantable medical devices, wherein at least a portion of the device is coated or impregnated with a compound of formula (I).

The invention further provides methods for determining whether or not a compound is a candidate for treating or preventing an infection caused by bacterium that uses 5'-methylthioadenosine deaminase (MTADA) in a quorum sensing pathway, the method comprising determining whether or not the compound inhibits MTADA, wherein a compound that inhibits MTADA is a candidate for treating or preventing an infection caused by bacterium that uses MTADA in a quorum sensing pathway and wherein a compound that does not inhibit MTADA is not a candidate for treating or preventing an infection caused by bacterium that uses MTADA in a quorum sensing pathway.

BRIEF DESCRIPTION OF THE DRAWINGS

FIG. 3. Sequence alignment of TmMTADA (2PLM) and putative MTADA sequences of *P. aeruginosa* PAO1. Based on the structural analysis of 2PLM, the residues interacting with Zn-, ribose-, adenine, and methylthio-groups are indicated, respectively in underlining, bold italic underlining, bold italic, and bold underlining. The two arginine residues of 2PLM are responsible for carboxylate binding of SAH and are indicated in double underlining. Sequences without interactions in the active site are not shown. Sequence ID Nos: PA0134 SEQ ID NO:1; PA1521—SEQ ID NO:2; PA0142—SEQ ID NO:3; PA3170—SEQ ID NO:4; 2PLM—SEQ ID NO:5; PA2499—SEQ ID NO:6: PA0437—SEQ ID NO:7; PA0148—SEQ ID NO:8; PA3480 SEQ ID NO:9.

FIG. 6. Stereoview of the catalytic site of PaMTADA containing MTCF, Zn ion, and the adjacent amino acids. The Zn ion and water are drawn as spheres. The hydrogen bonds between MTCF and surrounding environment are shown as dashed lines. The Zn chelating amino acid contacts are shown as dashed lines. The ligand/Zn-omit $F_o$-$F_c$ density map is shown as a mesh at a contour level of 5.0σ.

DETAILED DESCRIPTION OF THE INVENTION

Figure 1:
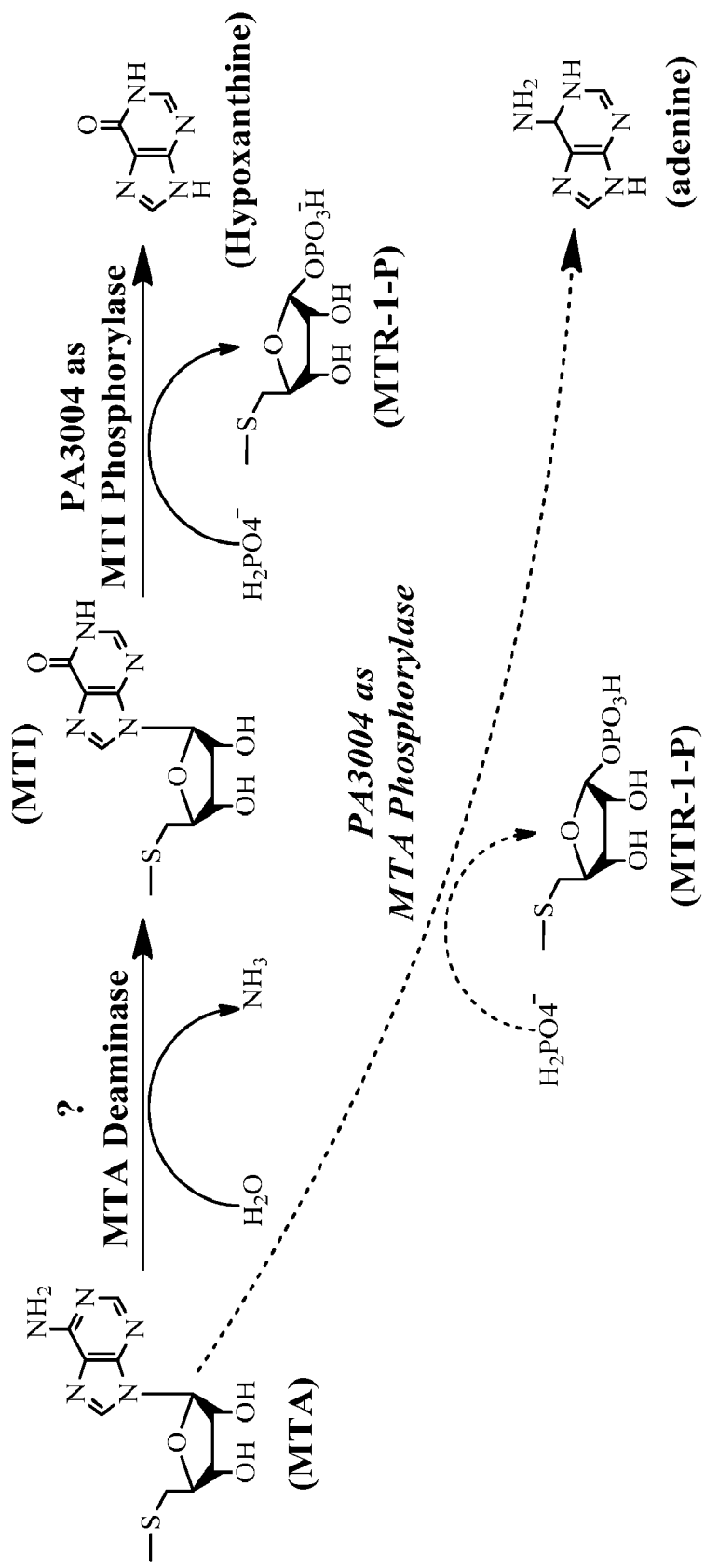
FIG. 1. MTA degradation in *Pseudomonas aeruginosa*. The dashed line indicates the previous (and incorrect) annotation of MTA phosphorylase activity for PA3004 (in italics). The PA3004 protein is now identified as a MTI phosphorylase and the conversion of MTA to MTI requires the existence of MTA deaminase (10).

The invention provides a method of treating or preventing a *Pseudomonas aeruginosa* (*P. aeruginosa*) infection in a subject comprising administering to the subject a compound of formula (I) in an amount effective to treat or prevent a *P. aeruginosa* infection in a subject, wherein formula (I) is

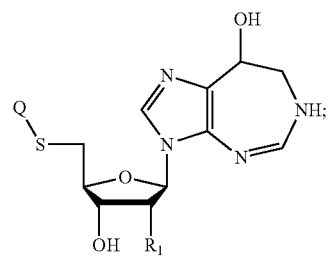

wherein R1 is H or OH; and wherein Q is C1-C6 alkyl, aryl or aralkyl, wherein Q is optionally substituted with one or more methyl, hydroxyl or halogen; or a pharmaceutically acceptable salt thereof or an ester thereof.

Q can be C1-C6 alkyl, and is preferably C1-C3 alkyl, i.e., a methyl, ethyl, or propyl group. More preferably, Q is methyl.

Q can be aryl. As used herein, the term "aryl" means an aromatic radical having 6 to 12 carbon atoms and includes heteroaromatic radicals. Preferred aryls include those having 6 carbon atoms, e. g., phenyl.

Q can also be an aralkyl. The term "aralkyl" means an alkyl radical having an aryl substituent. Preferably, the alkyl is C1-C3. Preferably, the aryl is phenyl.

Q can be substituted with one or more methyl, hydroxy or halogen, such as Cl, F, Br or I. Chlorine and fluorine are preferred halogens. The substitution can be at an ortho, meta or para position of an aryl or aralkyl.

Preferred compounds include those selected from the group consisting of

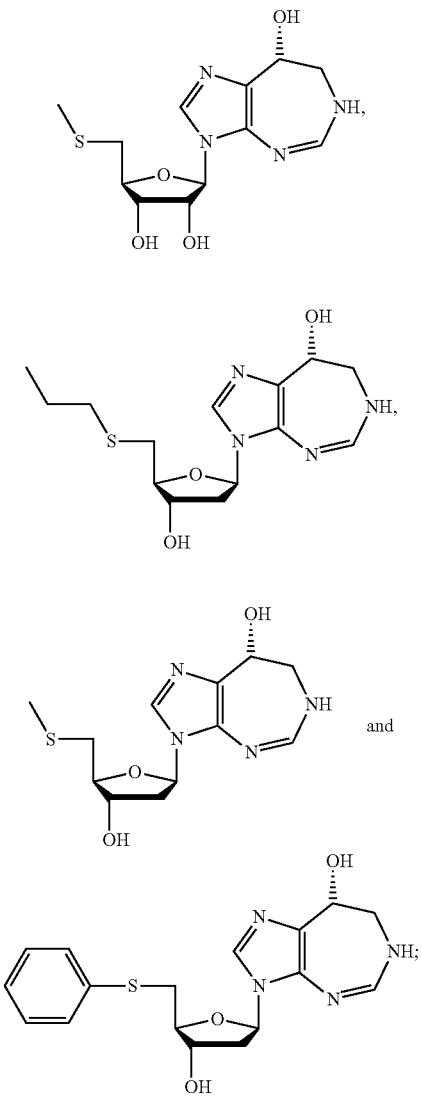

or a pharmaceutically acceptable salt thereof or an ester thereof.

More preferred compounds are

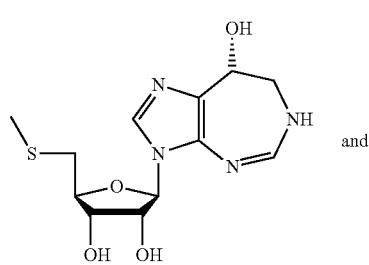

and

-continued

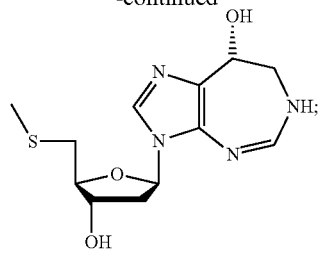

or a pharmaceutically acceptable salt thereof or an ester thereof.

Methods of preparing analogs of coformycin are described in U.S. Patent Application Publication No. US2009/0227532, published Sep. 10, 2009, the contents of which are incorporated herein by reference.

The term "pharmaceutically acceptable salts" includes non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

As used herein, to treat a *P. aeruginosa* bacterial infection in a subject means to reduce the virulence of the *P. aeruginosa* bacteria in the subject. The term *P. aeruginosa* "bacterial infection" shall mean any deleterious presence of *P. aeruginosa* bacteria in the subject.

The compounds of formula (I) of the present invention can also be used to treat a subject at risk for acquiring an infection due to *P. aeruginosa*, i.e., to prevent a *P. aeruginosa* infection in a subject. Subjects at risk for acquiring a *P. aeruginosa* infection include for example, but are not limited to, cystic fibrosis patients, neutropenic patients, patients with necrotising enterocolitis, burn victims, patients with wound infections, and patients in a hospital setting, in particular surgical patients and patients being treated using an implantable medical device such as a catheter.

The invention also provides an implantable medical device, wherein at least a portion of the device is coated, co-formulated or impregnated with a compound of formula (I)

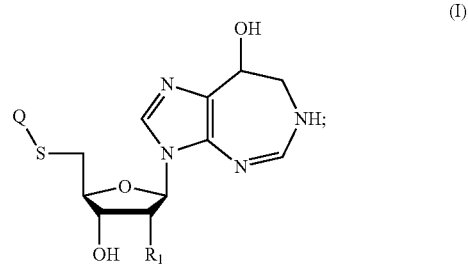

(I)

wherein R1 is H or OH; and wherein Q is C1-C6 alkyl, aryl or aralkyl, wherein Q is optionally substituted with one or more methyl, hydroxyl or halogen; or a pharmaceutically acceptable salt thereof or an ester thereof. The implantable medical device can be, for example, a catheter, a venous catheter, an arterial catheter, a transcutaneous catheter, a dialysis catheter, a urinary catheter, a tracheal catheter or a tracheal tube. The medical device can be, for example, for implantation in a blood vessel or a body cavity. Treatment and use of such medical devices can prevent biofilm formation and *P. aeruginosa* infection at the site where a subject is exposed to the device.

Preferably, the compound is administered to a subject or present in a composition or present in or on a medical device in an amount that is effective to inhibit *Pseudomonas aeruginosa* 5'-methylthioadenosine deaminase (MTADA). Preferably, the compound is administered or present in an amount that does not inhibit growth of *Pseudomonas aeruginosa*, i.e., the compound is administered or present in a "sub-growth inhibiting amount." Preferably, the compound is administered or present in an amount that is effective to inhibit quorum sensing in *Pseudomonas aeruginosa*.

The term "sub-growth inhibiting amount" of a compound as used herein means an amount of the compound, which when contacted with a population of *P. aeruginosa* bacteria, does not reduce the growth of the bacterial population. Preferably, the sub-growth inhibiting amount of the compound inhibits quorum sensing in the *P. aeruginosa* bacteria. Preferably, the sub-growth inhibiting amount of the compound is effective to reduce virulence of the *P. aeruginosa* bacteria without promoting the development of resistance by the *P. aeruginosa* bacteria to the compound.

The term "quorum sensing" as used herein refers to the process by which bacteria produce and detect signaling molecules with which to coordinate gene expression and regulate processes beneficial to the microbial community. The term "inhibit quorum sensing" as used herein means altering this process such that coordination of gene expression and process regulation in microbial communities are impaired or prevented.

The compound can be administered to a subject by routes known in the art, such as, e.g., orally, parenterally, by inhalation, topically, rectally, nasally, buccally or via an implanted reservoir. The compound can be administered by means of sustained release.

For oral administration, the compound can be formulated into solid or liquid preparations, for example tablets, capsules, powders, solutions, suspensions and dispersions. The compound can be formulated with agents such as, e.g., lactose, sucrose, corn starch, gelatin, potato starch, alginic acid and/or magnesium stearate.

The compounds may also be administered by injection in a physiologically acceptable diluent such as, e.g., water or saline. The diluent may comprise one or more other ingredients such as, e.g., ethanol, propylene glycol, an oil or a pharmaceutically acceptable surfactant.

The compounds may also be administered topically. Carriers for topical administration of the compounds of include, e.g., mineral oil, liquid petrolatum, white petrolatum, propylene glycol, polyoxyethylene, polyoxypropylene compound, emulsifying wax, sorbitan monostearate, polysorbate 60, cetyl ester wax, cetearyl alcohol, 2-octyldodecanol, benzyl alcohol and water.

The invention also provides compositions for treating or preventing a *Pseudomonas aeruginosa* (*P. aeruginosa*) infection in a subject comprising a compound of formula (I) in an amount effective to treat or prevent a *P. aeruginosa* infection in a subject and a pharmaceutically acceptable carrier, wherein formula (I) is

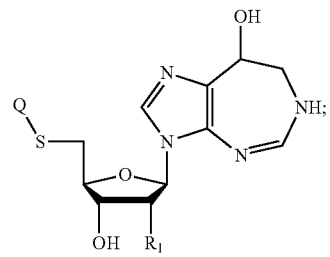

wherein R1 is H or OH; and wherein Q is C1-C6 alkyl, aryl or aralkyl, wherein Q is optionally substituted with one or more methyl, hydroxyl or halogen; or a pharmaceutically acceptable salt thereof or an ester thereof.

As used herein, a "pharmaceutically acceptable carrier" is (i) compatible with the other ingredients of the composition without rendering the composition unsuitable for its intended purpose, and (ii) suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include any of the standard pharmaceutical carriers such as phosphate buffered saline solutions, water, and emulsions such as oil/water emulsions and microemulsions.

The invention further provides for the use a compound of formula (I) for the preparation of a medicament for treating or preventing a *P. aeruginosa* infection. The invention still further provides a compound of formula (I) for use for treating or preventing a *P. aeruginosa* infection.

The invention further provides a method for determining whether or not a compound is a candidate for treating or preventing an infection caused by bacterium that uses 5'-methylthioadenosine deaminase (MTADA) in a quorum sensing pathway, the method comprising determining whether or not the compound inhibits MTADA, wherein a compound that inhibits MTADA is a candidate for treating or preventing an infection caused by bacterium that uses MTADA in a quorum sensing pathway and wherein a compound that does not inhibit MTADA is not a candidate for treating or preventing an infection caused by bacterium that uses MTADA in a quorum sensing pathway. Examples of bacterium include species of *Pseudomonas*, such as *Pseudomonas aeruginosa*. Examples of methods of determining whether or not a compound inhibits MTADA are described and illustrated herein.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Overview

*Pseudomonas aeruginosa* possesses an unusual metabolic pathway for 5'-methylthioadenosine (MTA) involving deamination to 5'-methylthioinosine (MTI) followed by N-ribosyl phosphorolysis to hypoxanthine and 5-methylthio-α-D-ribose 1-phosphate. The specific MTI phosphorylase of *P. aeruginosa* has been reported (10). The present studies characterized MTA deaminase from *P. aeruginosa* (PaMTADA). Genomic analysis indicated the PA3170 locus to be a candidate for MTA deaminase (MTADA). Protein encoded by PA3170 was expressed and shown to deaminate MTA and adenosine, with 40-fold greater catalytic efficiency for MTA. The $k_{cat}/K_m$ value of $1.6 \times 10^7$ $M^{-1}s^{-1}$ for MTA is the highest catalytic efficiency known for an adenosine or an MTA deaminase. 5'-Methylthiocoformycin (MTCF) is a 4.8 pM transition state analogue causing no significant inhibition of human adenosine deaminase or MTA phosphorylase. MTCF is permeable to *P. aeruginosa* and exhibits an $IC_{50}$ of 3 nM on cellular PaMTADA activity. PaMTADA is the only activity in *P. aeruginosa* extracts to act on MTA. MTA and 5-Methylthio-α-D-ribose are involved in quorum sensing pathways; thus, PaMTADA is a potential target for quorum sensing. Distinct pathways in *P. aeruginosa* may confer specificity. The crystal structure of PaMTADA in complex with MTCF shows the transition state mimic 8-R-hydroxyl group in contact with a catalytic site $Zn^{2+}$, the 5'-methylthio group in a hydrophobic pocket and the NH transition state mimic of the diazepine ring in contact with a catalytic site Glu.

Materials and Methods

Figure 2:
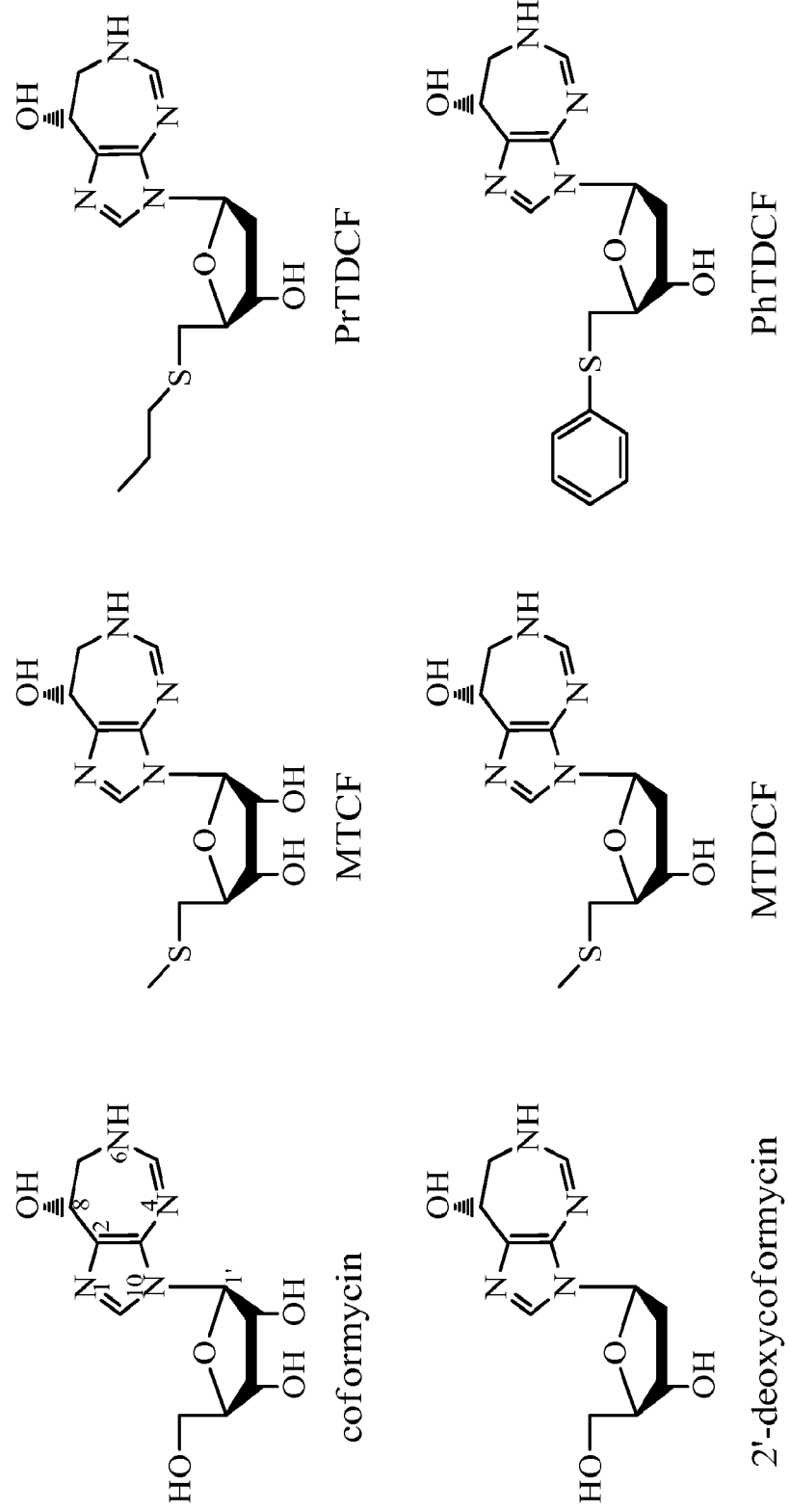
FIG. 2. Inhibitors of PaMTADA. Coformycin and 2'-deoxycoformycin are transition state analogues of adenosine deaminase. MTCF and other 5'-functionalized-2'-deoxycoformycins are transition state analogues of MTA deaminases (15).

Chemicals. Coformycin (CF), 5'-methylthiocoformycin (MTCF), 2'-deoxycoformycin (DCF), 5'-methylthio-2'-deoxycoformycin (MTDCF), 5'-propylthio-2'-deoxycoformycin (PrTDCF) and 5'-phenylthio-2'-deoxycoformycin (PhTDCF) were synthesized by methods reported earlier (FIG. 2) (15). [8-$^{14}$C]MTA was synthesized as described previously (16). All other chemicals and reagents were obtained from Sigma or Fisher Scientific, and were of reagent grade.

Plasmid construction. A synthetic gene was designed from the predicated protein sequence of gene PA3170 in *Pseudomonas* Genome Database (17). Gene PA3170 belongs to *Pseudomonas aeruginosa* PAO1 and encodes a conserved hypothetical protein. The synthetic gene was purchased from DNA2.0 Inc. in a pJexpress414 expression vector. The encoded protein has an additional 14 amino acids at the N-terminus which includes a His$_6$ tag.

Enzyme purification and preparation. BL21-CodonPlus (DE3)-RIPL *E. coli* were transformed with the synthetic plasmid and grown overnight at 37° C. in 100 mL of LB medium with 100 µg/mL Ampicillin. The culture was transferred into 1 L of LB/Ampicillin medium and growth continued at 37° C. to an O.D.$_{600}$ of 0.7. Expression was induced for 4 hours at 37° C. by addition of 1 mM IPTG. The cells were harvested by centrifugation at 4500 g for 30 min. The cell pellet was suspended in 20 mL of 15 mM imidazole, 300 mM NaCl, and 50 mM phosphate, pH 8.0 (lysis buffer), with addition of 2 tablets of EDTA-free protease inhibitor (from Roche Diagnostics) and 20 mg lysozyme (from chicken egg). Cells were disrupted by two passes through a French pressure cell and centrifuged at 20,000 g for 30 min. The supernatant was loaded onto a 4 mL column of Ni-NTA Superflow resin equilibrated with 5 columns of lysis buffer. The column was washed with 5 volumes of 50 mM imidazole, 300 mM NaCl, and 50 mM phosphate, pH 8.0 (wash buffer), and the target protein was eluted with 3 volumes of 250 mM imidazole, 300 mM NaCl, and 50 mM phosphate, pH 8.0 (elution buffer). Eluted protein was immediately dialyzed against 300 mM NaCl, 10% glycerol, and 50 mM phosphate, pH 8.0 to remove the imidazole, followed by dialysis against 10% glycerol, and 50 mM Hepes, pH 7.4. The purified protein was concentrated to 7.8 mg/ml and was >95% pure as judged by SDS-PAGE. Protein was stored at −80° C. The extinction coefficient of PaMTADA is 48.93 $mM^{-1}$ $cm^{-1}$ at 280 nm, as calculated by the ProtParam program from ExPASy and was used to estimate protein concentration (ca.expasy.org/seqanalref).

Enzymatic assays. Deaminase activity on MTA, adenosine, SAH, and adenine was measured by the absorbance change at 265 nm. The extinction coefficients are 8.1 $mM^{-1}cm^{-1}$ for MTA and adenosine (14), and 6.7 $mM^{-1}cm^{-1}$ for SAH and adenine (20). Deaminase activity on guanosine was measured at 260 nm with an extinction coefficient of 3.9 $mM^{-1}cm^{-1}$ (18). HsMTAP and EcMTAN activity on MTA was determined by conversion of product adenine to 2,8-dihydroxyadenine using xanthine oxidase as the coupling enzyme (19). The extinction coefficient is 15.5 $mM^{-1}cm^{-1}$ at 305 nm. Reactions of deaminase were carried out at 25° C. in 1 cm cuvettes. Assay mixtures of 1 mL contained 50 mM Hepes, pH 7.4, 100 mM NaCl, 100 µg/mL BSA, variable concentrations of substrate, and appropriate amounts of purified PaMTADA. Reactions were initiated by addition of enzyme and the initial rates were monitored with a CARY 300 UV-Visible spectrophotometer. Control rates (no PaMTADA) were subtracted from initial rates. Kinetic parameters of PaMTADA were obtained by fitting initial rates to the Michaelis-Menten equation using GraFit 5 (Erithacus Software).

Inhibition assays. Inhibition assays for PaMTADA were carried out by adding 0.15 nM PaMTADA into reaction mixtures at 25° C. containing 50 mM Hepes, pH 7.4, 100 mM NaCl, 100 µM MTA, 100 µg/mL BSA, and variable concentrations of inhibitor. Inhibition assays of HsMTAP were carried out at 25° C. by adding 0.8 nM enzyme into reaction mixtures containing 50 mM Hepes, pH 7.4, 100 mM phosphate, pH 7.4, 100 µM MTA, 1 mM DTT, 1 unit of XOD, and variable concentrations of MTCF. Inhibition assays of EcMTAN were carried out at 25° C. by adding 0.15 nM enzyme into reaction mixtures containing 100 mM Hepes, pH 7.4, 100 mM NaCl, pH 7.4, 50 µM MTA, 1 mM DTT, 1 unit of XOD, and variable concentrations of MTCF. Controls having no enzyme and no inhibitor were included in all of the inhibition assays. The inhibition constant was obtained by fitting initial rates with variable inhibitor concentrations to equation (1) using GraFit 5 (Erithacus Software):

$$\frac{v_i}{v_o} = \frac{[S]}{K_m + [S] + \frac{K_m[I]}{K_i}} \quad (1)$$

where $v_i$ is the initial rate in the presence of inhibitor, $v_o$ is the initial rate in the absence of inhibitor, $K_m$ is the Michaelis constant for MTA, [S] and [I] are MTA and inhibitor concentrations, respectively, and $K_i$ is the inhibition constant. The inhibitor concentration was corrected using equation (2) when it was less than 10 times of the enzyme concentration (20):

$$[I]' = [I] - \left(1 - \frac{v_i}{v_o}\right)E_t \quad (2)$$

where [I]' is the effective inhibitor concentration, [I] is the inhibitor concentration in the reaction mixture, $E_t$ is the total enzyme concentration.

Crystallization, data collection, and structure determination of PaMTADA in complex with MTCF. To obtain the PaMTADA:MTCF complex, the PaMTADA was concentrated to 35 mg/ml in 50 mM Hepes, pH 7.5, and 10% glycerol followed by incubation with 1.2 mM MTCF. The PaMTADA:MTCF complex crystallized in 1.26 M sodium phosphate (monobasic) and 0.14 M potassium phosphate (dibasic) at a final pH of 5.6 at 18° C. using hanging drop or sitting drop vapor diffusion method. Crystals were transferred to mother liquor supplemented with 20% glycerol and flash-cooled in liquid $N_2$ prior to data collection. X-ray diffraction data were collected at the X29A beamline of Brookhaven National Laboratory on an ADSC Q315 detector at 100K. Data were processed using HKL2000 program suite and summarized in Table 1 (21).

The structure of PaMTADA:MTCF complex was determined by molecular replacement with the program Molrep (22), using the crystal structure of the amidohydrolase family protein OLEI061672_1_465 from *Oleispira antarctica* (PDB ID: 3LNP), without bound ligand as the search model. Models without inhibitor were iteratively rebuilt in COOT and refined in Refmac5 (23, 24). Manual inhibitor building was initiated only after the $R_{free}$ decreased below 30% and was guided by clear ligand density in $F_o$-$F_c$ electron density maps contoured at 3σ. Data processing and refinement statistics are summarized in Table 1.

Inhibition of cellular PaMTADA activity. Inhibition of PaMTADA activity in cell lysates was carried out as follows. *P. aeruginosa* PAO1 (ATCC number: 15692) was grown at 37° C. to stationary phase in LB medium for 16 hours. Cells were collected by centrifugation at 16,100 g and washed three times with 100 mM phosphate, pH 7.4. Cells were lysed using BugBuster reagent (Novagen). Cleared lysate (47 µL) was incubated with and without 1-1000 nM of MTCF and [8-$^{14}$C]MTA (15 µL containing approximately 0.1 µCi $^{14}$C) in 100 mM phosphate, pH 7.4, for 20 min, with a total volume of 80 µL. Reaction mixtures were quenched with perchloric acid (1.8 M final concentration) and neutralized with potassium hydroxide. Precipitates were removed by centrifugation and carrier hypoxanthine, adenine, MTI, and MTA were added to the supernatant. Separation of the metabolites was carried out on a $C_{18}$ Luna HPLC column (Phenomenex) with a gradient of 5 to 52.8% acetonitrile in 20 mM triethylamine acetate, pH 5.2. The UV absorbance at 260 nm was monitored. The retention times were 5.1 min (hypoxanthine), 7.5 min (adenine), 20.4 min (MTI), and 21.9 min (MTA), respectively. Fractions were collected in scintillation vials, dried, reconstituted in 200 µL deionized water prior to addition of 10 mL ULTIMA GOLD LSC-Cocktail scintillation fluid. The cpm of $^{14}$C was counted at 20 min per cycle for three cycles using a Tri-Carb 2910TR liquid scintillation analyzer. Cell lysate was replaced by lysis buffer in reaction mixtures in control experiments. Inhibition of cellular PaMTADA was investigated with addition of MTCF to the LB medium instead of addition to the cell lysate. The final concentrations of MTCF used in the LB varied from 0 to 1000 nM. Culture growth in the presence of MTCF used 1% inoculums by volume in all cultures. All other procedures were the same as described above. A third experiment was carried out with addition of 500 nM MTCF in LB medium and addition of 0 or 100 nM MTCF to the cell lysate after the BugBuster lysis. The $IC_{50}$ for MTCF was obtained by fitting the percentage of degraded MTA to the concentration of MTCF using equation (4) and the GraFit 5 (Erithacus Software):

$$y = y_0 - \left(\frac{c[I]}{IC_{20} + [I]}\right) \quad (4)$$

where y is the percentage of degraded MTA at certain [I] (inhibitor concentration), $y_0$ is the percentage of degraded MTA at zero [I], c is the maximum difference between y and $y_0$, and $IC_{50}$ is the inhibitor concentration giving half maximal inhibition.

Results and Discussion

The hunt for PaMTADA. There is no gene annotated as MTA deaminase in *Pseudomonas*, but the previous discovery of the pathway from MTA to hypoxanthine via MTI indicated the existence of a MTA deaminase in *P. aeruginosa* (10). The active site of MTA deaminase was expected to contain Zinc, purine and methylthioribose binding sites. The *Pseudomonas* genome database contains several genes annotated as deaminases based on Zinc binding motif. These included PA0134 (guanine deaminase), PA1521 (guanine deaminase), PA0142 (guanine deminse), PA0148 (adenosine deaminase), PA2499 (unspecified deaminse), PA3480 (deoxycytidine triphosphate deaminase), PA0437 (cytosine deaminase), and PA3170 (guanine deaminase). All of the corresponding protein sequences were searched against the PDB database. One of the hits was MTA deaminase from *Thermotoga maritima* (TmMTADA; PDB ID: 1J6P). TmMTADA also deaminates SAH and adenosine but favors MTA as the substrate (14). The crystal structure (PDB ID: 2PLM) of TmMTADA in complex with S-inosyl homocysteine (SIH) revealed catalytic site residues for recognition of ribosyl and homocysteine moieties of SIH. Glu84 interacts with the ribosyl group by forming two hydrogen bonds with 2' and 3' hydroxyl group. Met114, Try115, and Phe116 create a hydrophobic pocket surrounding the methylthio group of homocysteine. Arg136 and Arg148 are involved in the binding of carboxylate group of homocysteine. Multiple sequence alignments show Glu84, Met114, Try115 and Phe116 to be conserved in PA3170 but Arg136 and Arg148 are not (FIG. 3). His173 and Glu203 of TmMTADA interact with the adenine base and are conserved in PA3170. The analysis supports assignment of PA3170 as a MTA deaminase with differences in the ability to use SAH as a substrate.

MTA deaminase activity of PA3170. The recombinant PA3170 protein was purified and tested for substrate specificity (Table 2). The recombinant protein deaminated MTA and adenosine but was inactive with adenine, SAH and guanosine, suggesting a high specificity for both sugar and purine base. MTA is the most favorable substrate with a $k_{cat}$ of 24.6 s$^{-1}$ and $K_m$ of 1.5 µM ($k_{cat}/K_m$ of $1.6 \times 10^7$ M$^{-1}$s$^{-1}$). The enzyme is less efficient with adenosine. Although the $k_{cat}$ is 17 s$^{-1}$, the $K_m$ of 46 µM is 30 times higher than that for MTA, causing most of the 40-fold lower catalytic efficiency ($k_{cat}/K_m$) on adenosine ($3.7 \times 10^5$ M$^{-1}$s$^{-1}$.) The 30-fold lower $K_m$ with MTA supports an important role of the 5'-methylthio-group for MTA binding. The substrate specificity reveals PA3170 protein to be a specific MTA deaminase. The catalytic efficiency of $1.6 \times 10^7$ M$^{-1}$s$^{-1}$ is the highest of known adenosine or MTA deaminase reactions.

Deaminase activity on MTA has been reported in malarial ADAs and *T. maritime* MTADA (12-14). The known MTADA enzymes have catalytic efficiency in the range of $1.4 \times 10^4$ M$^{-1}$s$^{-1}$ to $1.4 \times 10^5$ M$^{-1}$s$^{-1}$, which are over 100-fold less than that of PaMTADA. Their catalytic efficiency on adenosine is also low and comparable with the ability of PaMTADA to use adenosine, in the range of $9.2 \times 10^3$ M$^{-1}$s$^{-1}$ to $8.2 \times 10^4$ M$^{-1}$s$^{-1}$. Human and bovine ADAs do not utilize MTA as substrate and their $k_{cat}/K_m$ values for adenosine are $1.6 \times 10^6$ M$^{-1}$s$^{-1}$ and $1.1 \times 10^6$ M$^{-1}$s$^{-1}$, respectively (12, 15). PaMTADA has a similar $k_{cat}/K_m$ values on adenosine as other ADAs, suggesting this enzyme has the catalytic capacity to act as both ADA and MTADA in biological conditions.

Expression of PaMTADA supports the catabolism of MTA in P. aeruginosa in the two step pathway of MTA→MTI→hypoxanthine that was proposed recently on the basis of the existence of MTI phosphorylase and the catabolism of $^{14}$C-labeled MTA (10).

Picomolar inhibitors of PaMTADA. Coformycin (CF) and 2'-deoxycoformycin (DCF) are natural product transition state analogue inhibitors of adenosine deaminases with picomolar affinity (25). Their 8-R-hydroxyl group mimics the attacking hydroxyl group at the transition state and the 7-membered diazepine ring is protonated at N6, which mimics the N1 protonation proposed to occur with adenosine or MTA at the transition state (26). The molecular electrostatic potential surfaces of the coformycins closely resemble the geometry and charge distribution of the transition states of adenosine deaminases from human, bovine, and Plasmodim falciparum. MTCF and MTDCF possess the transition state features of coformycin and the unique substrate specificity determinants of this enzyme for the 5'-methylthio group (15). MTCF and MTDCF were originally developed as transition-state analogue inhibitors of PfADA, involved in both adenosine and MTA deamination and a potential target for purine salvage in malaria (12). MTCF and MTDCF inhibit PfADA with equilibrium dissociation constants of 400 pM and 700 pM, respectively, but they have no inhibitory effect on human ADA. Inhibition of human ADA is known to cause central nervous system dysfunction and the genetic deficiency of human ADA causes severe immune deficiency disorders (27-29).

Six coformycin-based transition state analogue inhibitors (FIG. 2) were tested with PaMTADA and gave $K_i$ values ranging from 4.8 pM to 90 nM (Table 3). Coformycin inhibits PaMTADA with a $K_i$ value of 90 nM. MTCF, however, exhibits more potent inhibition with a 4.8 pM dissociation constant. Thus, MTCF binds to PaMTADA 18,800 times better than CF, and 312,500 times better than the substrate MTA as judged by $K_m/K_i$. The 2'-hydroxyl group has a small effect on the affinity of CF and MTCF. 2'-Deoxycoformycin and MTDCF have $K_i$ values of 37 nM and 8 pM, respectively. Coformycins are transition state analogue for adenosine deaminases, while MTCF is specific for MTA deaminase. PaMTADA has 30 times higher affinity and 40 times higher catalytic efficiency for MTA than for adenosine, which contributes to the more potent inhibition of MTCF than CF. However, the difference in inhibitor affinity is 18,800 times, which cannot be solely attributed to the difference in substrate specificity of the enzymes. The MTCF appears to more precisely capture the transition state features of PaMTADA. Since the transition state features on the purine base are similar in CF and MTCF, the 5'-methylthio group is likely to play a critical role in organizing the substrate and enzyme to an efficient geometry resembling the transition state. However, a detailed transition state structure for PaMTADA has not yet been established. 5'-Propylthiol-2'-deoxycoformycin (PrTDCF) binds PaMTADA 8 times weaker than MTDCF with a $K_i$ value of 67 pM. Similarly, PhTDCF binds 16 times weaker with a $K_i$ value of 130 pM. These results suggest that PaMTADA can accommodate larger hydrophobic group at the 5'-position of the inhibitor, but prefers the methylthio group.

Inhibitor specificity of PaMTADA can be compared to that of PfADA since both enzymes have adenosine and MTA deaminase activities. MTCF, MTDCF, PrTDCF, and PhTDCF bind PfADA with respective $K_i$ values of 400 pM, 700 pM, 12 nM, and 60 nM, representing 5, 9, 150, and 750 times weaker binding affinity than that of CF for the same enzyme (15). 2'-Deoxycoformycin binds slightly tighter than CF with a $K_i$ of 38 pM. The preference of PfADA for binding of CF and DCF relative to MTCF and other 5'-functionalized-2'-deoxycoformycins are the opposite of that found for PaMTADA. This establishes the distinct substrate specificity preferences for adenosine and MTA with these enzymes. PfADA prefers adenosine and PaMTADA prefers MTA. In addition, MTCF and 5'-functionalized-2'-deoxycoformycins bind PaMTADA more tightly than PfADA, suggested by the >80-fold lower $K_i$, which may be attributed to the 160 times higher catalytic efficiency of PaMTADA on MTA than that of PfADA. Binding of transition state analogues is proportional to catalytic rate enhancement, and the behavior of PaMTADA provides another example of this phenomenon. The preference of MTCF and 5'-functionalized-2'-deoxycoformycins as transition state analogue inhibitor of PaMTADA emphasizes substrate specificity as an essential factor in inhibitor design in addition to transition state features.

MTCF and other 5'-functionalized-2'-deoxycoformycins have no inhibitory effects on human ADA, suggesting an approach to target P. aeruginosa with minimal side effects to human hosts. MTCF was examined to test if it might be metabolized by other enzymes related to MTA metabolism, namely by human MTA phosphorylase (MTAP) and E. coli MTA nucleosidase (MTAN). No significant degradation of MTCF was observed for either of these enzymes ($k_{obs}$<0.001 s$^{-1}$).

MTCF was tested for its ability to inhibit human MTAP and E. coli MTAN. MTCF binds to human MTAP 625,000 times weaker than to PaMTADA, with a $K_i$ of 3 μM. The $K_i$ of E. coli MTAN is >5 μM. These results demonstrate the high specificity of MTCF for MTADA activity with minimal interactions with related enzymes.

Figures 4A, 4B, 4C:
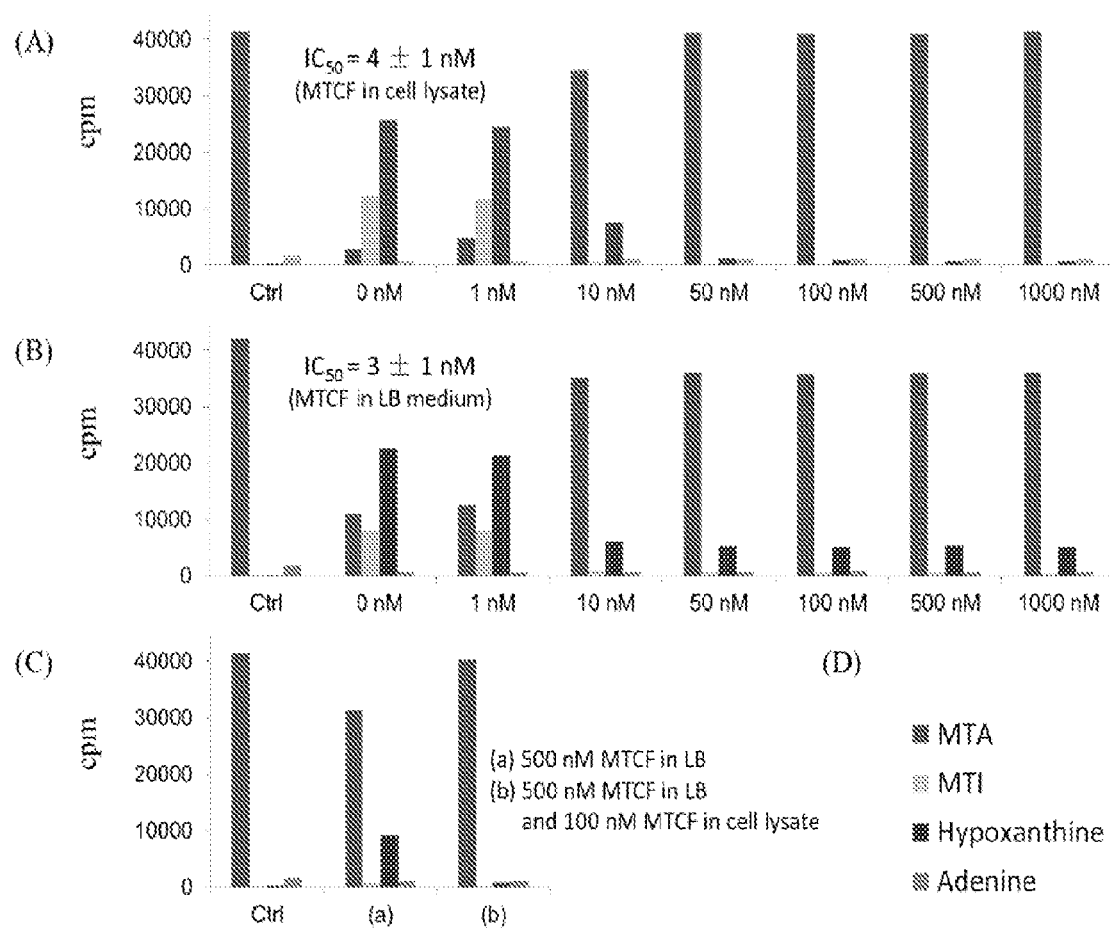
FIG. 4A-4C. Cellular PaMTADA activity and inhibition by MTCF. (A) Effect of MTCF on MTA metabolism in *P. aeruginosa* cell lysate. (B) Effect of MTCF in *P. aeruginosa* cell cultures (grown in LB medium). (C) Effect of MTCF in *P. aeruginosa* cell lysate (grown in LB medium containing MTCF). The activity of PaMTADA was monitored by the degradation of [8-$^{14}$C]MTA. Related $^{14}$C-metabolites were purified using HPLC and quantitated by scintillation counting. $IC_{50}$ values were calculated using concentrations of MTCF and the percentage of degraded [8-$^{14}$C]MTA (D) Code for the metabolites, from left to right in each cluster of 4 columns: MTA, MTI, Hypoxanthine, Adenine.

Inhibition of cellular PaMTADA activity. MTCF exhibits tight binding to PaMTADA in enzymatic assays with a 4.8 pM dissociation constant. Its inhibition of PaMTADA was tested in intact P. aeruginosa cells and cell lysate. The inhibition was evaluated by the decrease of MTA degradation. MTA degradation was monitored by tracking the decrease of $^{14}$C-label in [8-$^{14}$C]MTA or its increase in hypoxanthine, adenine, and MTI. Varied concentrations of MTCF were added to P. aeruginosa cell lysates (FIG. 4A). In the absence of MTCF, conversion of [8-$^{14}$C]MTA to downstream metabolites was nearly complete, indicating that PaMTADA and PaMTIP are functional under these experimental conditions. The degradation of MTA was completely blocked at 50 nM inhibitor, indicating that the deamination of MTA is the only pathway for MTA catabolism in P. aeruginosa extracts. The IC$_{50}$ was 4 nM, demonstrating the inhibitory potency of MTCF in whole cell lysates.

The cellular permeability and in vivo inhibition of PaMTADA by MTCF was examined by the effect of the inhibitor added to LB medium during cell growth (FIG. 4B). The growth of P. aeruginosa PAO1 was monitored with or without MTCF (up to 1 μM) for 36 hours at 37° C. There was no effect of MTCF on cell growth based on OD$_{600}$ values. Cells were harvested, wash free of exogenous inhibitor and PaMTADA activity determined by [8-$^{14}$C]MTA metabolism in cell extracts. MTA metabolism was clearly inhibited at the PaMTADA step by the growth of cells in the presence of MTCF in LB medium. Maximal inhibition was achieved at a concentration of 10 nM MTCF. However, a small, residual PaMTADA activity was observed independent of the MTCF concentration during growth, even at 1 μM. Two hypotheses were considered for this activity. First, growth on MTCF may induce a deaminase activity resistant to MTCF. Second, the residual activity might arise from diffusional release of the inhibitor during the dilution (and incubation) of a small volume of cell extract into the larger volume of lysis buffer and other incubation buffer. To test these hypotheses, cells were cultured as above in LB medium containing 500 nM MTCF. After preparation of cell extracts at the start of the MTA degradation experiment, either 0 or 100 nM MTCF was added and the degradation of the [8-$^{14}$C]MTA was monitored (FIG. 4C). If the residual PaMTADA activity arises from a resistant deaminase, the degradation of [8-$^{14}$C] MTA would be unchanged. If the residual MTA metabolism is due to diffusional loss of inhibitor during extract work-up and incubation, addition of inhibitor in cell lysate would completely quench the residual activity. All PaMTADA activity was inhibited in the experiment. Thus, the residual activity of PaMTADA, clearly present before addition of MTCF to the cell lysate, is a result of slow diffusional loss of inhibitor from the enzyme in cell lysate. Correcting for this residual activity, the $IC_{50}$ of PaMTADA in LB medium was then calculated to be 3 nM, similar to the 4 nM $IC_{50}$ of MTCF in cell lysate. These results indicate that MTCF is permeable to *P. aeruginosa* cells. The cellular PaMTADA concentration can also be estimated in the range of 10-50 nM as this concentration of MTCF is required to titrate extracts to zero catalytic activity.

Figures 5A, 5B:
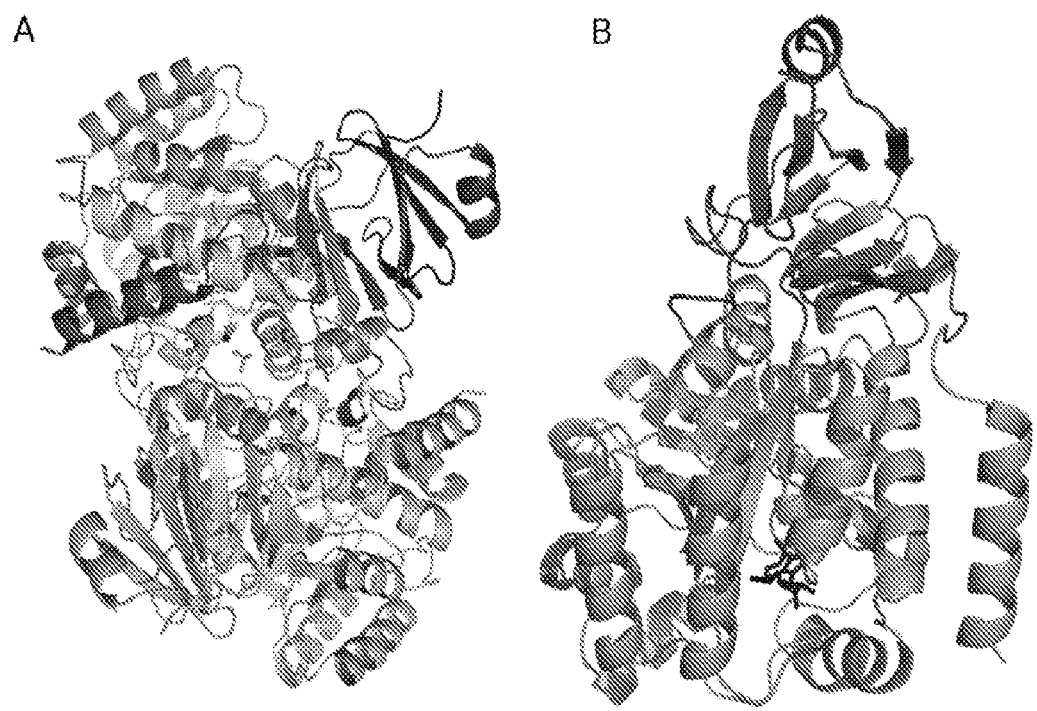
FIG. 5A-5B. The structure of PaMTADA. (A) The homodimeric PaMTADA is shown. The Zn ions are shown as spheres and phosphate as sticks. (B) Two distinct domains are present in the PaMTADA monomers. MTCF is drawn as a black stick model to show the position of the active site.

The structure of PaMTADA and MTCF interaction. The crystal structure of PaMTADA in complex with MTCF was determined to 2.0 Å resolution. PaMTADA forms a homodimer with two zinc ions and two phosphate ions located at the dimer interface (FIG. 5a). The N-terminal 14 amino acids include the $His_6$ tag, are disordered and are distant from the active site. The protein folds into two domains. The core of the larger domain consists of an $(\alpha/\beta)_8$ TIM barrel, whereas the smaller domain, including the first 67 amino acid residues and the residues from 361 to 419, is organized into a β sandwich (FIG. 5b).

Figure 7:
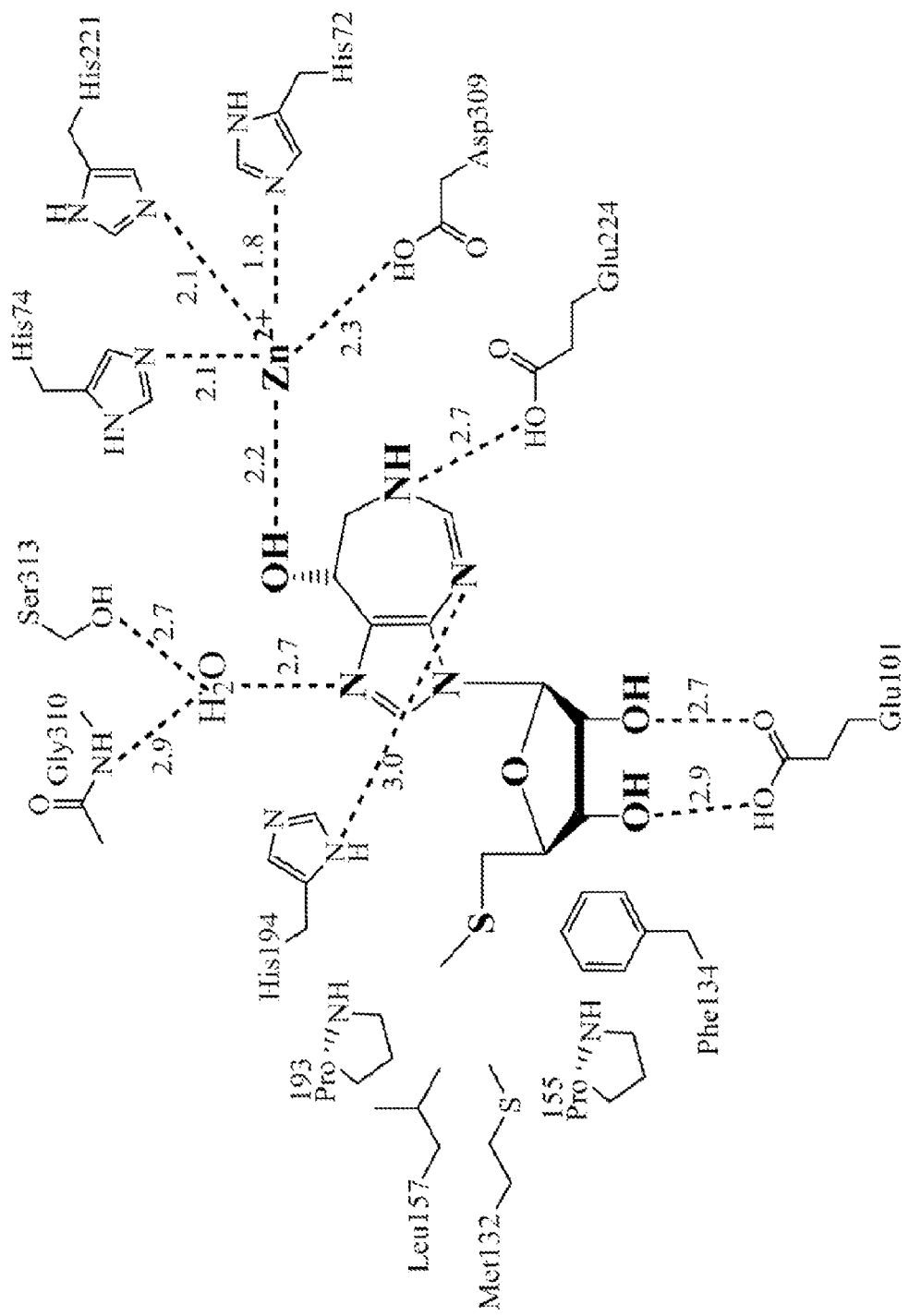
FIG. 7. 2D Distance map of PaMTADA active site. The hydrogen bonds and ionic interactions in the active site are shown as dashed lines. Distances are in angstroms.

The 8-(R)-hydroxydiazepine moiety of MTCF mimics some features of the transition state for N6-deamination of the adenine base. The 8-(R)-hydroxy group at a $sp^3$-bonded center of MTCF mimics the nucleophilic water adding to the $sp^2$ C6 center of the purine ring to create a $sp^3$ transition state. The structure of PaMTADA resembles that of the *Plasmodium vivax* ADA:MTCF complex reported earlier, where, the N1, N4 and N6 of diazepine ring form hydrogen bonds with surrounding residues or a water molecule (FIGS. 6,7) (13). The N1 forms hydrogen bonds to the amide of Gly310 and the side chain of Ser313 via a water molecule. The N4 and N6 form hydrogen bonds to side chains of His194 and Glu224, respectively. Both 2' and 3' hydroxyl groups of ribose moiety form hydrogen bonds with the side chain of Glu101, consistent with other structures and the predicted sequence analysis (FIG. 6). The 5'-methylthio group resides in a hydrophobic pocket surrounded by Met132, Phe134, Pro155, Leu157, Pro193 and His194 (FIG. 6), explaining the binding advantage afforded by the 5'-methylthio group in MTCF compared to the 5'-hydroxyl group in CF. Transition state features of MTCF include the protonation at N6 and the (R)-hydroxyl with $sp^3$ geometry at C8. The protonated N6 mimics the transition state and forms a hydrogen bond with Glu224 and (R)-hydroxyl group forms an ionic bond with the Zn ion, a mimic of the Zn—OH$^-$ nucleophile at the transition state of the normal aromatic nucleophilic substitution reaction. These interactions from the transition state features provide significant binding energy to the inhibitor and thus contribute to the 4.8 pM affinity of MTCF.

Implications for Quorum Sensing. Six transition state analogue inhibitors have been identified for PaMTADA with picomolar dissociation constants. MTCF is the most potent inhibitor with a 4.8 pM $K_i$ in in vitro assays and an $IC_{50}$ of 3 nM in in vivo studies. It is specific to the MTA deminase activity and has no significant inhibitory effects on human ADA and human MTAP. MTCF is thus a suitable candidate for blocking PaMTADA activity. In *P. aeruginosa*, MTA degradation follows a unique two-step pathway of MTA→MTI→hypoxanthine, where MTADA is the only enzyme responsible for the first step. Most bacteria utilize MTA nucleosidase for MTA degradation, catalyzing the hydrolysis of MTA to adenine. Inhibition of PaMTADA is expected to increase cellular MTA level and block quorum sensing of *P. aeruginosa*, similar to the effects of MTAN inhibition in other bacteria. This study assigns the identity of the PA3170 protein as an unusual and specific MTADA and confirms the two-step pathway of MTA metabolism in *P. aeruginosa*. Transition state analogue inhibitors are identified for PaMTADA with powerful activity and cellular permeability to provide new tools to disrupt QS in *P. aeruginosa* and other organisms with this unusual pathway.

TABLE 1

Data collection and refinement statistics.

| | PaMTADA:MTCF complex |
|---|---|
| PDB code | 4GBD |
| Data collection | |
| Space group | C2 |
| Cell dimension | |
| a, b, c (Å) | 119.8, 120.3, 77.3 |
| α, β, γ (°) | 90.0, 108.0, 90.0 |
| Resolutions (Å) | 50.00-2.00 (2.07-2.00) |
| $R_{sym}$ (%) | 9.0 (65.6) |
| I/σI | 11.5 (1.7) |
| Completeness (%) | 97.6 (98.3) |
| Redundancy | 3.7 (3.6) |
| Refinement | |
| Resolution (Å) | 50.00-2.00 |
| No. unique reflections | 70236 |
| $R_{work}/R_{free}$ (%) | 19.6/23.5 |
| B-factors (Å$^2$) | |
| Protein | |
| (main chain) | 40.8 |
| (side chain) | 46.2 |
| Water | 44.5 |
| Ligand | 42.3 |
| No. of Atoms | |
| Protein | 6694 |
| Water | 243 |
| Ligand | 44 |
| R.m.s deviations | |
| Bond lengths (Å) | 0.012 |
| Bond angles (°) | 1.61 |
| Ramanchran analysis | |
| favored region | 96.5% |
| allowed region | 3.1% |

TABLE 1-continued

Data collection and refinement statistics.

| PDB code | PaMTADA:MTCF complex 4GBD |
|---|---|
| disallowed region | 0.4% |
| Coordinate Error by Luzzati plot (Å) | 0.24 |

Numbers in parentheses are for the highest-resolution shell. One crystal was used for each data set.

TABLE 2

Substrate Specificity of PaMTADA, PfADA, and Human ADA on Adenosine and MTA.

| | adenosine | | | MTA | | |
|---|---|---|---|---|---|---|
| Enzyme | $k_{cat}$ ($s^{-1}$) | $K_m$ ($\mu M$) | $k_{cat}/K_m$ ($\times 10^5\ M^{-1}s^{-1}$) | $k_{cat}$ ($s^{-1}$) | $K_m$ ($\mu M$) | $k_{cat}/K_m$ ($\times 10^5\ M^{-1}s^{-1}$) |
| PaMTADA | 17 ± 1 | 46 ± 8 | 3.7 ± 0.7 | 24.6 ± 0.8 | 1.5 ± 0.3 | 160 ± 30 |
| PfADA [a] | 1.8 ± 0.1 | 29 ± 3 | 0.62 ± 0.07 | 15.0 ± 0.9 | 170 ± 20 | 0.9 ± 0.1 |
| Human ADA [a] | 36 ± 1 | 22 ± 3 | 16 ± 2 | <0.02 | NA | NA |

[a] PfADA and human ADA values are from Ting et al. and Tyler et al., respectively (12, 15).
[b] PaMTADA shows no activity on adenine, guanosine or SAH ($k_{obs}$ < 0.001 $s^{-1}$).

TABLE 3

Summary of $K_i$ values for PaMTADA, PfADA, and human ADA

| | Inhibitors | | |
|---|---|---|---|
| | PaMTADA $K_i$ (nM) [b] | PfADA [a] $K_i$ (nM) [b] | Human ADA [a] $K_i$ (nM) [b] |
| Coformycin (CF) | 90 ± 10 | 0.08 ± 0.02 | 0.11 ± 0.02 |
| DCF | 37 ± 1 | 0.038 ± 0.009 | 0.026 ± 0.005 |
| MTCF | 0.0048 ± 0.0005 | 0.4 ± 0.1 | >10000 |
| MTDCF | 0.0080 ± 0.0004 | 0.7 ± 0.2 | >10000 |
| PrTDCF | 0.067 ± 0.005 | 12 ± 1 | >10000 |
| PhTDCF | 0.130 ± 0.009 | 60 ± 10 | >10000 |

[a] The $K_i$ values of PfADA and human ADA are from Tyler et al. (15).
[b] $K_i$ is an equilibrium dissociation constant. It is the $K_i$ in competitive inhibition and $K_i$* in slow-onset inhibition.

REFERENCES

1. Bodey, G. P., Bolivar, R., Fainstein, V., and Jadeja, L. (1983) Infections caused by *Pseudomonas aeruginosa*, *Rev. Infect. Dis.* 5, 279-313.
2. Van Delden, C., and Iglewski, B. H. (1998) Cell-to-cell signaling and *Pseudomonas aeruginosa* infections, *Emerg. Infect. Dis.* 4, 551-560.
3. Strateva, T., and Yordanov, D. (2009) *Pseudomonas aeruginosa*—a phenomenon of bacterial resistance, *J. Med. Microbiol.* 58, 1133-1148.
4. Waters, C. M., and Bassler, B. L. (2005) Quorum sensing: cell-to-cell communication in bacteria, *Annu. Rev. Cell. Dev. Biol.* 21, 319-346.
5. Rumbaugh, K. P., Griswold, J. A., and Hamood, A. N. (2000) The role of quorum sensing in the in vivo virulence of *Pseudomonas aeruginosa, Microbes Infect* 2, 1721-1731.
6. Kohler, T., Guanella, R., Carlet, J., and van Delden, C. (2010) Quorum sensing-dependent virulence during *Pseudomonas aeruginosa* colonisation and pneumonia in mechanically ventilated patients, *Thorax* 65, 703-710.
7. Smith, R. S., and Iglewski, B. H. (2003) *Pseudomonas aeruginosa* quorum sensing as a potential antimicrobial target, *J. Clin. Invest.* 112, 1460-1465.
8. Gutierrez, J. A., Crowder, T., Rinaldo-Matthis, A., Ho, M.-C., Almo, S. C., and Schramm, V. L. (2009) Transition state analogs of 5'-methylthioadenosine nucleosidase disrupt quorum sensing, *Nat. Chem. Biol.* 5, 251-257.
9. Buckoreelall, K., Wilson, L., and Parker, W. B. (2011) Identification and characterization of two adenosine phosphorylase activities in *Mycobacterium smegmatis, J. Bacteriol.* 193, 5668-5674.
10. Guan, R., Ho, M. C., Almo, S. C., and Schramm, V. L. (2011) Methylthioinosine phosphorylase from *Pseudomonas aeruginosa*. Structure and annotation of a novel enzyme in quorum sensing, *Biochemistry.* 50, 1247-1254.
11. Parsek, M. R., Val, D. L., Hanzelka, B. L., Cronan, J. E., Jr., and Greenberg, E. P. (1999) Acyl homoserine-lactone quorum-sensing signal generation, *Proc. Natl. Acad. Sci. U.S.A.* 96, 4360-4365.
12. Ting, L.-M., Shi, W., Lewandowicz, A., Singh, V., Mwakingwe, A., Birck, M. R., Ringia, E. A. T., Bench, G., Madrid, D. C., Tyler, P. C., Evans, G. B., Furneaux, R. H., Schramm, V. L., and Kim, K. (2005) Targeting a Novel *Plasmodium falciparum* Purine Recycling Pathway with Specific Immucillins, *J. Biol. Chem.* 280, 9547-9554.
13. Ho, M.-C., Cassera, M. B., Madrid, D. C., Ting, L.-M., Tyler, P. C., Kim, K., Almo, S. C., and Schramm, V. L. (2009) Structural and Metabolic Specificity of Methylthiocoformycin for Malarial Adenosine Deaminases, *Biochemistry.* 48, 9618-9626.
14. Hermann, J. C., Marti-Arbona, R., Fedorov, A. A., Fedorov, E., Almo, S. C., Shoichet, B. K., and Raushel, F. M. (2007) Structure-based activity prediction for an enzyme of unknown function, *Nature* 448, 775-U772.
15. Tyler, P. C., Taylor, E. A., Froehlich, R. F. G., and Schramm, V. L. (2007) Synthesis of 5'-Methylthio Coformycins: Specific Inhibitors for Malarial Adenosine Deaminase, *J. Am. Chem. Soc.* 129, 6872-6879.
16. Singh, V., Lee, J. E., Nunez, S., Howell, P. L., and Schramm, V. L. (2005) Transition state structure of 5'-methylthioadenosine/S-adenosylhomocysteine nucleosidase from *Escherichia coli* and its similarity to transition state analogues, *Biochemistry.* 44, 11647-11659.
17. Winsor, G. L., Lam, D. K., Fleming, L., Lo, R., Whiteside, M. D., Yu, N. Y., Hancock, R. E., and Brinkman, F. S. (2011) *Pseudomonas* Genome Database: improved comparative analysis and population genomics capability for *Pseudomonas* genomes, *Nucleic Acids Res* 39, D596-600.

18. Zielke, C. L., and Suelter, C. H. (1971) Purine, purine nucleoside, and purine nucleotide aminohydrolases, *Enzymes*, 3rd Ed. 4, 47-78.
19. Kung, P.-P., Zehnder, L. R., Meng, J. J., Kupchinsky, S. W., Skalitzky, D. J., Johnson, M. C., Maegley, K. A., Ekker, A., Kuhn, L. A., Rose, P. W., and Bloom, L. A. (2005) Design, synthesis, and biological evaluation of novel human 5'-deoxy-5'-methylthioadenosine phosphorylase (MTAP) substrates, *Bioorg. Med. Chem. Lett.* 15, 2829-2833.
20. Morrison, J. F., and Walsh, C. T. (1988) The behavior and significance of slow-binding enzyme inhibitors, *Adv. Enzymol. Relat. Areas Mol. Biol.* 61, 201-301.
21. Otwinowski, Z., and Minor, W. (1997) Processing of X-ray diffraction data collected in oscillation mode, *Macromolecular Crystallography, Pt A* 276, 307-326.
22. (1994) The CCP4 suite: programs for protein crystallography, *Acta Crystallogr D Biol Crystallogr* 50, 760-763.
23. Emsley, P., and Cowtan, K. (2004) Coot: model-building tools for molecular graphics, *Acta Crystallogr D Biol Crystallogr* 60, 2126-2132.
24. Potterton, E., Briggs, P., Turkenburg, M., and Dodson, E. (2003) A graphical user interface to the CCP4 program suite, *Acta Crystallogr D Biol Crystallogr* 59, 1131-1137.
25. Agarwal, R. P. (1982) Inhibitors of adenosine deaminase, *Pharmacol. Ther.* 17, 399-429.
26. Luo, M., Singh, V., Taylor, E. A., and Schramm, V. L. (2007) Transition-State Variation in Human, Bovine, and *Plasmodium falciparum* Adenosine Deaminases, *J. Am. Chem. Soc.* 129, 8008-8017.
27. Margolis, J., and Greyer, M. R. (2000) Pentostatin (Nipent): a review of potential toxicity and its management, *Semin. Oncol.* 27, 9-14.
28. Johnson, S. A. (2000) Clinical pharmacokinetics of nucleoside analogues: focus on haematological malignancies, *Clin. Pharmacokinet.* 39, 5-26.
29. Cristalli, G., Costanzi, S., Lambertucci, C., Lupidi, G., Vittori, S., Volpini, R., and Camaioni, E. (2001) Adenosine deaminase: functional implications and different classes of inhibitors, *Med. Res. Rev.* 21, 105-128.

---

What is claimed is:

1. A method of treating a *Pseudomonas aeruginosa* (*P. aeruginosa*) infection in a subject or treating a subject who is at risk for acquiring an infection due to *P. aeruginosa* comprising administering to the subject a compound of formula (I) in an amount effective to treat a *P. aeruginosa* infection in a subject or to treat a subject who is at risk for acquiring an infection due to *P. aeruginosa*, wherein formula (I) is

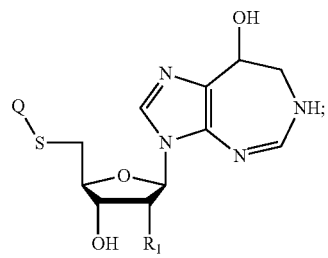

wherein R1 is H or OH; and
wherein Q is C1-C6 alkyl, aryl or aralkyl, wherein Q is optionally substituted with one or more methyl, hydroxyl or halogen;
or a pharmaceutically acceptable salt thereof or an ester thereof.

2. The method of claim 1, wherein Q is C1-C3 alkyl.
3. The method of claim 1, wherein Q is methyl.
4. The method of claim 1, wherein Q is phenyl.
5. The method of claim 1, wherein R1 is H.
6. The method of claim 1, wherein R1 is OH.
7. The method of claim 1, wherein the compound is selected from the group consisting of

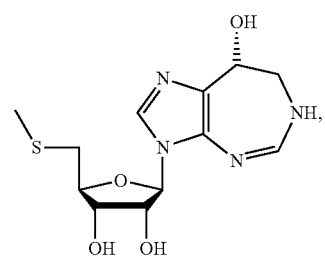

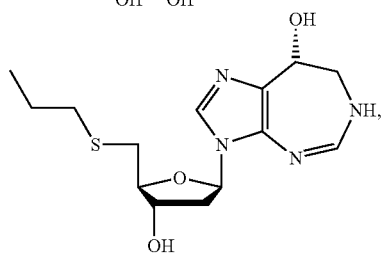

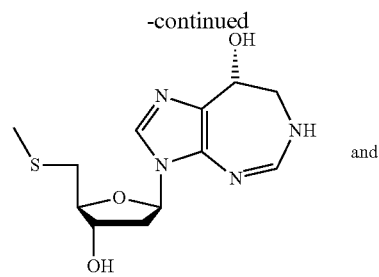

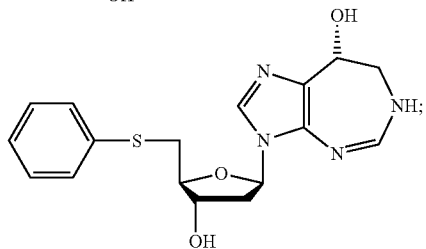

or a pharmaceutically acceptable salt thereof or an ester thereof.

8. The method of claim 1, wherein the compound is

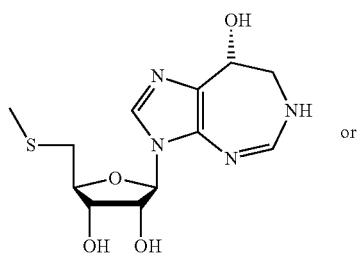

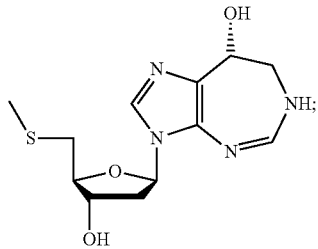

or a pharmaceutically acceptable salt thereof or an ester thereof.

9. The method of claim 1, wherein the compound is administered in an amount that is effective to inhibit *Pseudomonas aeruginosa* 5'-methylthioadenosine deaminase (MTADA).

10. The method of claim 1, wherein the compound is administered in an amount that does not inhibit growth of *Pseudomonas aeruginosa*.

11. The method of claim 1, wherein the compound is administered in an amount that is effective to inhibit quorum sensing in *Pseudomonas aeruginosa*.

12. The method of claim 1 for treating a *P. aeruginosa* infection in a subject.

13. The method of claim 1 for treating a subject who is at risk for acquiring an infection due to *P. aeruginosa*.

14. A composition for treating a *Pseudomonas aeruginosa* (*P. aeruginosa*) infection in a subject or for treating a subject who is at risk for acquiring an infection due to *P. aeruginosa*, the composition comprising a compound of formula (I) in an amount effective to treat a *P. aeruginosa* infection in a subject or to treat a subject who is at risk for acquiring an infection due to *P. aeruginosa*, and a pharmaceutically acceptable carrier,
wherein formula (I) is

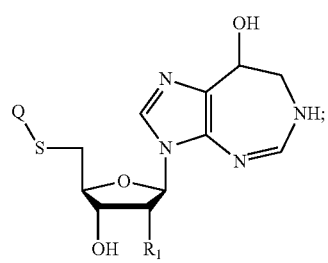

wherein R1 is H or OH; and
wherein Q is C1-C6 alkyl, aryl or aralkyl, wherein Q is optionally substituted with one or more methyl, hydroxyl or halogen;
or a pharmaceutically acceptable salt thereof or an ester thereof.

15. The composition of claim 14, wherein the compound is selected from the group consisting of

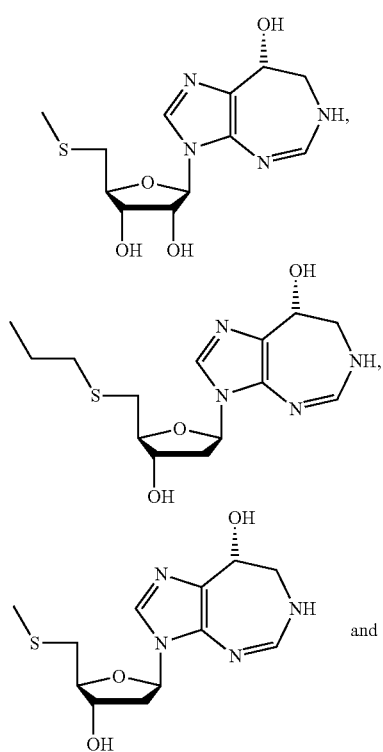

and

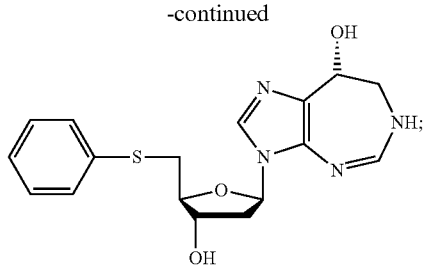

or a pharmaceutically acceptable salt thereof or an ester thereof.

16. The composition of claim 14, wherein the compound is

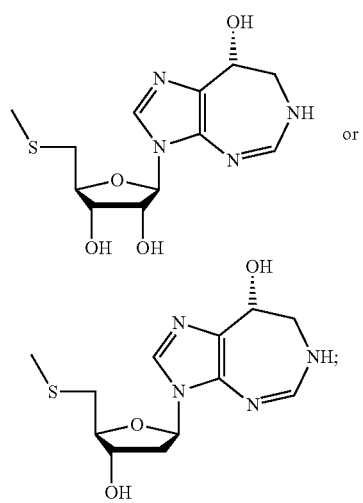

or a pharmaceutically acceptable salt thereof or an ester thereof.

17. An implantable medical device, wherein at least a portion of the device is coated or impregnated with a compound of formula (I) in an amount effective to treat a *P. aeruginosa* infection in a subject or to treat a subject who is at risk for acquiring an infection due to *P. aeruginosa*,
wherein formula (I) is

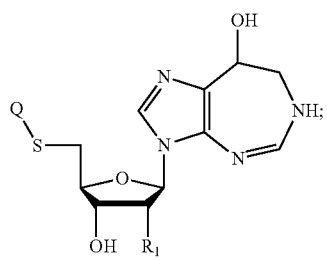

wherein R1 is H or OH; and
wherein Q is C1-C6 alkyl, aryl or aralkyl, wherein Q is optionally substituted with one or more methyl, hydroxyl or halogen;
or a pharmaceutically acceptable salt thereof or an ester thereof.

18. The implantable medical device of claim 17, wherein the device is a catheter, a venous catheter, an arterial catheter, a transcutaneous catheter, a dialysis catheter, a urinary catheter, a tracheal catheter or a tracheal tube.

19. The implantable medical device of claim 17, wherein the device is for implantation in a blood vessel or a body cavity.

\* \* \* \* \*

SEQUENCE LISTING

```
<160> NUMBER OF SEQ ID NOS: 9

<210> SEQ ID NO 1
<211> LENGTH: 275
<212> TYPE: PRT
<213> ORGANISM: Pseudomonas aeruginosa

<400> SEQUENCE: 1

Glu His Gly His Val Arg Ala Leu Asp His Ala Thr Tyr Leu Leu Pro
1               5                   10                  15

Gln Leu Pro Ala Asp Leu Pro Leu Glu Glu His Pro Gln Arg Leu Leu
            20                  25                  30

Leu Pro Gly Phe Val Asp Cys His Val His Tyr Pro Gln Leu Gly Val
        35                  40                  45

Ile Ala Ser Tyr Gly Thr Gln Leu Leu Asp Trp Leu Glu Thr His Thr
    50                  55                  60

Phe Pro Ala Glu Gln Arg Phe Ala Asp Ala Gly Tyr Ala Ala Ala Gln
65                  70                  75                  80

Ala Glu Leu Phe Leu Asp Glu Leu Leu Arg His Gly Thr Thr Thr Ala
                85                  90                  95

Leu Val Phe Gly Thr Val His Ala Val Ser Ala Glu Ala Phe Phe Gln
            100                 105                 110

Ala Ala Gln Lys Arg Arg Leu Arg Met Ile Ala Gly Lys Val Leu Met
        115                 120                 125

Asp Arg Asn Ala Pro Pro Ala Leu Cys Asp Thr Ala Ala Ser Gly Tyr
    130                 135                 140

Ala Glu Ser Arg Ala Leu Ile Glu Arg Trp His Gly Asn Gly Arg Leu
145                 150                 155                 160

Gln Tyr Ala Val Thr Pro Arg Phe Ala Pro Thr Ser Ser Pro Glu Gln
                165                 170                 175

Leu Ala Ala Ala Ala Arg Leu Leu Asp Glu Tyr Pro Gly Val Tyr Leu
            180                 185                 190

His Thr His Leu Ser Glu Asn Leu Lys Glu Val Ala Trp Val Gly Glu
        195                 200                 205

Leu Phe Pro Gln Ala Gln Asp Tyr Leu Asp Val Tyr His Arg Asp Leu
    210                 215                 220
```

```
Asp Gly Leu Val Gly Asn Phe Leu Pro Gly Arg Glu Ala Asp Phe Val
225                 230                 235                 240

Ala Leu Asp Leu Ala Ala Thr Pro Met Ile Ala Gln Arg Met Glu His
            245                 250                 255

Ala Arg Gly Leu Ala Asp Thr Leu Phe Val Leu Asn Thr Leu Gly Asp
            260                 265                 270

Asp Arg Ala
        275

<210> SEQ ID NO 2
<211> LENGTH: 274
<212> TYPE: PRT
<213> ORGANISM: Pseudomonas aeruginosa

<400> SEQUENCE: 2

Glu Asp Gly Lys Val Ala Arg Leu Gly Asp Ala Glu Thr Leu Leu Gly
1               5                   10                  15

Glu Ile Gly Glu Val Glu Val Phe Glu Tyr Arg Asp Ala Leu Ile Thr
            20                  25                  30

Pro Gly Phe Ile Asp Thr His Ile His Phe Pro Gln Thr Gly Met Ile
            35                  40                  45

Ala Ser Tyr Gly Glu Gln Leu Leu Asp Trp Leu Asn Thr Tyr Thr Phe
50                  55                  60

Pro Thr Glu Arg Gln Phe Gly Asp Gln Ala His Ala Asp Gln Val Ala
65                  70                  75                  80

Glu Ile Phe Leu Gln Glu Leu Leu Arg Asn Gly Thr Thr Thr Ala Leu
            85                  90                  95

Val Phe Gly Ser Val His Arg Gln Ser Val Glu Ser Leu Phe Glu Ala
            100                 105                 110

Ala Arg Arg Leu Asp Leu Arg Leu Ile Ala Gly Lys Val Met Met Asp
            115                 120                 125

Arg Asn Ala Pro Asp Tyr Leu Thr Asp Thr Ala Glu Ser Ser Tyr Arg
130                 135                 140

Asp Ser Lys Ala Leu Ile Glu Arg Trp His Gly Gln Gly Arg Leu Leu
145                 150                 155                 160

Tyr Ala Val Thr Pro Arg Phe Ala Pro Thr Ser Thr Ala Glu Gln Leu
            165                 170                 175

Asp Met Ala Ala Arg Leu Leu Arg Glu His Pro Gly Val Tyr Leu His
            180                 185                 190

Thr His Leu Ser Glu Asn Leu Lys Glu Ile Glu Trp Val Lys Glu Leu
            195                 200                 205

Phe Pro Glu Arg Ser Gly Tyr Leu Asp Val Tyr Asp His Glu Leu Asp
210                 215                 220

Asp Arg Ile Gly Ser Phe Ala Thr Ser Asn Glu Ala Asp Phe Val Val
225                 230                 235                 240

Leu Asp Tyr His Ala Thr Pro Leu Leu Ser Tyr Arg Leu Ser Gln Ala
            245                 250                 255

Gly Ser Leu Ala Glu Arg Leu Phe Ala Leu Thr Ile Leu Gly Asp Asp
            260                 265                 270

Arg Thr

<210> SEQ ID NO 3
<211> LENGTH: 289
<212> TYPE: PRT
<213> ORGANISM: Pseudomonas aeruginosa
```

<400> SEQUENCE: 3

Glu Asp Gly Arg Ile Val Glu Leu Leu Gly Ala Gly Gln Gln Pro Ala
1               5                   10                  15

Gln Pro Cys Ala Ser Gln Phe Asp Ala Ser Arg His Val Val Leu Pro
            20                  25                  30

Gly Leu Val Asn Thr His His Phe Tyr Gln Thr Leu Thr Arg Ala
        35                  40                  45

Trp Ala Pro Val Val Asn Gln Pro Leu Phe Pro Trp Leu Lys Thr Leu
    50                  55                  60

Tyr Pro Val Trp Ala Arg Leu Thr Pro Glu Lys Leu Glu Leu Ala Thr
65                  70                  75                  80

Lys Val Ala Leu Ala Glu Leu Leu Ser Gly Cys Thr Thr Ala Ala
                85                  90                  95

Asp His His Tyr Leu Phe Pro Gly Gly Leu Gln Ala Ile Asp Val
                100                 105                 110

Gln Ala Gly Val Val Glu Glu Leu Gly Met Arg Ala Met Leu Thr Arg
            115                 120                 125

Gly Ser Met Ser Leu Gly Glu Lys Asp Gly Gly Leu Pro Pro Gln Gln
    130                 135                 140

Thr Val Gln Glu Ala Glu Thr Ile Leu Ala Asp Ser Glu Arg Leu Ile
145                 150                 155                 160

Ala Arg Tyr His Gln Arg Gly Asp Gly Ala Arg Val Gln Ile Ala Leu
                165                 170                 175

Ala Pro Cys Ser Pro Phe Ser Val Thr Pro Glu Ile Met Arg Ala Ser
            180                 185                 190

Ala Glu Val Ala Ala Arg His Asp Val Arg Leu His Thr His Leu Ala
        195                 200                 205

Glu Thr Leu Asp Glu Glu Asp Phe Cys Leu Gln Arg Phe Gly Leu Arg
    210                 215                 220

Thr Val Asp Tyr Leu Asp Ser Gly Arg Ser Asp Ile Gly Glu Leu Ala
225                 230                 235                 240

Pro Gly Lys Gln Ala Asp Leu Ala Leu Phe Lys Leu Asp Glu Leu Arg
                245                 250                 255

Phe Ser Gly Ser His Asp Pro Leu Ser Ala Leu Leu Leu Cys Ala Ala
            260                 265                 270

Asp Arg Ala Asp Arg Val Met Val Gly Gly Ala Trp Arg Val Val Asp
        275                 280                 285

Gly

<210> SEQ ID NO 4
<211> LENGTH: 272
<212> TYPE: PRT
<213> ORGANISM: Pseudomonas aeruginosa

<400> SEQUENCE: 4

Arg Asp Gly Gln Ile Ala Leu Val Ala Pro Arg Glu Gln Ala Met Arg
1               5                   10                  15

His Gly Ala Thr Glu Ile Arg Glu Leu Pro Gly Met Leu Leu Ala Pro
            20                  25                  30

Gly Leu Val Asn Ala His Gly His Ser Ala Met Ser Leu Phe Arg Gly
        35                  40                  45

Leu Ala Asp Asp Leu Pro Leu Met Thr Trp Leu Gln Asp His Ile Trp
    50                  55                  60

Pro Ala Glu Gly Gln Trp Val Ser Glu Asp Phe Ile Arg Asp Gly Thr

```
                65                  70                  75                  80
        Glu Leu Ala Ile Ala Glu Gln Val Lys Gly Gly Ile Thr Cys Phe Ser
                            85                  90                  95

Asp Met Tyr Phe Tyr Pro Gln Ala Ile Cys Gly Val Val His Asp Ser
                            100                 105                 110

Gly Val Arg Ala Gln Val Ala Ile Pro Val Leu Asp Phe Pro Ile Pro
                            115                 120                 125

Gly Ala Arg Asp Ser Ala Glu Ala Ile Arg Gln Gly Met Ala Leu Phe
                    130                 135                 140

Asp Asp Leu Lys His His Pro Arg Ile Arg Ile Ala Phe Gly Pro His
        145                 150                 155                 160

Ala Pro Tyr Thr Val Ser Asp Asp Lys Leu Glu Gln Ile Leu Val Leu
                            165                 170                 175

Thr Glu Glu Leu Asp Ala Ser Ile Gln Met His Val His Glu Thr Ala
                            180                 185                 190

Phe Glu Val Glu Gln Ala Met Glu Arg Asn Gly Glu Arg Pro Leu Ala
                    195                 200                 205

Arg Leu His Arg Gly Leu Glu Arg Leu Ile Gly Ser Leu Glu Ala Gly
                    210                 215                 220

Lys Ala Ala Asp Leu Val Ala Phe Asp Leu Ser Gly Leu Ala Gln Gln
        225                 230                 235                 240

Pro Val Tyr Asp Pro Val Ser Gln Leu Ile Tyr Ala Ser Gly Arg Asp
                            245                 250                 255

Cys Val Arg His Val Trp Val Gly Gly Arg Gln Leu Leu Asp Asp Gly
                            260                 265                 270

<210> SEQ ID NO 5
<211> LENGTH: 250
<212> TYPE: PRT
<213> ORGANISM: Thermotoga maritima

<400> SEQUENCE: 5

Glu Asn Gly Thr Ile Lys Arg Val Leu Gln Gly Glu Val Lys Val Asp
        1                   5                   10                  15

Leu Asp Leu Ser Gly Lys Leu Val Met Pro Ala Leu Phe Asn Thr His
                            20                  25                  30

Thr His Ala Pro Met Thr Leu Leu Arg Gly Val Ala Glu Asp Leu Ser
                            35                  40                  45

Phe Glu Glu Trp Leu Phe Ser Lys Val Leu Pro Ile Glu Asp Arg Leu
                    50                  55                  60

Thr Glu Lys Met Ala Tyr Tyr Gly Thr Ile Leu Ala Gln Met Glu Met
        65                  70                  75                  80

Ala Arg His Gly Ile Ala Gly Phe Val Asp Met Tyr Phe His Glu Glu
                            85                  90                  95

Trp Ile Ala Lys Ala Val Arg Asp Phe Gly Met Arg Ala Leu Leu Thr
                            100                 105                 110

Arg Gly Leu Val Asp Ser Asn Gly Asp Asp Gly Arg Gly Leu Glu Glu
                    115                 120                 125

Asn Leu Lys Leu Tyr Asn Glu Trp Asn Gly Phe Glu Gly Arg Ile Phe
                    130                 135                 140

Val Gly Phe Gly Pro His Ser Pro Tyr Leu Cys Ser Glu Glu Tyr Leu
        145                 150                 155                 160

Lys Arg Val Phe Asp Thr Ala Lys Ser Leu Asn Ala Pro Val Thr Ile
                            165                 170                 175
```

```
His Leu Tyr Glu Thr Ser Lys Glu Glu Tyr Asp Leu Glu Asp Ile Leu
                180                 185                 190

Asn Gly Phe Lys Ser Gly Lys Ile Glu Glu Gly Trp Asn Ala Asp Leu
            195                 200                 205

Val Val Ile Asp Leu Asp Leu Pro Glu Met Phe Pro Val Gln Asn Ile
        210                 215                 220

Lys Asn His Leu Val His Ala Phe Ser Gly Glu Val Phe Ala Thr Met
225                 230                 235                 240

Val Ala Gly Lys Trp Ile Tyr Phe Asp Gly
                245                 250

<210> SEQ ID NO 6
<211> LENGTH: 61
<212> TYPE: PRT
<213> ORGANISM: Pseudomonas aeruginosa

<400> SEQUENCE: 6

Met Ser Asp Glu Thr Phe Met Arg Glu Ala Ile Ala Leu Ala Arg Ala
1               5                   10                  15

Asn Val Glu Ala Gly Gly Arg Pro Phe Gly Ala Val Leu Val Arg Asp
            20                  25                  30

Gly Arg Val Leu Ala Arg Gly Val Asn Gln Ile His Glu Thr His Asp
        35                  40                  45

Pro Ser Gly Leu Tyr Arg Gln Trp Arg Gln Arg Gln Ala
    50                  55                  60

<210> SEQ ID NO 7
<211> LENGTH: 275
<212> TYPE: PRT
<213> ORGANISM: Pseudomonas aeruginosa

<400> SEQUENCE: 7

Ala Asp Gly Arg Ile Ala Ala Leu Val Pro Met Glu Gln Ala Ala Asp
1               5                   10                  15

Asp Ala Gly Glu Arg Leu Asp Gly Ala Gly Leu Ala Val Pro Pro
            20                  25                  30

Phe Ile Glu Pro His Val His Leu Asp Thr Thr Gln Thr Ala Gly Gln
        35                  40                  45

Pro Glu Trp Asn Arg Ser Gly Thr Leu Phe Glu Gly Ile Glu Arg Trp
    50                  55                  60

Ala Gln Arg Lys Ala Leu Leu Ser His Glu Asp Val Lys Gln Arg Ala
65                  70                  75                  80

Trp Gln Thr Leu Lys Trp Gln Ile Ala Asn Gly Val Gln His Val Arg
                85                  90                  95

Ser His Val Asp Val Ser Asp Pro Thr Leu Thr Ala Leu Lys Ala Met
            100                 105                 110

Leu Glu Val Arg Gly Glu Val Ala Pro Trp Val Asp Leu Gln Ile Val
        115                 120                 125

Ala Phe Pro Gln Glu Gly Ile Leu Ser Tyr Pro Asn Gly Leu Glu Leu
    130                 135                 140

Leu Glu Glu Ser Leu Arg Leu Gly Ala Asp Val Val Gly Ala Ile Pro
145                 150                 155                 160

His Phe Glu Phe Thr Arg Glu Leu Gly Val Glu Ser Leu His Lys Ala
                165                 170                 175

Ile Asp Leu Ala Lys Arg Tyr Asp Leu Pro Val Asp Val His Cys Asp
            180                 185                 190
```

```
Glu Ile Asp Asp Glu Gln Ser Arg Phe Leu Glu Thr Leu Ala Met Leu
            195                 200                 205

Ala His Arg Asp Gly Leu Gly Ala Arg Gly Leu Arg Glu Tyr Gly Ile
210                 215                 220

Glu Val Gly His Pro Ala Asn Leu Leu Val Leu Pro Ala Arg Asp Gly
225                 230                 235                 240

Phe Asp Ala Val Arg Arg Gln Val Pro Val Arg Tyr Ser Ile Arg Gly
                245                 250                 255

Gly Arg Leu Leu Ala Glu Thr Val Pro Ala Gln Thr Thr Val Phe Leu
            260                 265                 270

Glu Gln Ala
        275

<210> SEQ ID NO 8
<211> LENGTH: 190
<212> TYPE: PRT
<213> ORGANISM: Pseudomonas aeruginosa

<400> SEQUENCE: 8

Met Tyr Glu Trp Leu Asn Ala Leu Pro Lys Ala Glu Leu His Leu His
1               5                   10                  15

Leu Glu Gly Thr Leu Glu Pro Glu Leu Leu Phe Ala Leu Ala Glu Arg
            20                  25                  30

Asn Arg Ile Ala Leu Pro Trp Asn Asp Val Glu Thr Leu Arg Lys Ala
        35                  40                  45

Tyr Ala Phe Asn Asn Leu Gln Glu Phe Leu Asp Leu Tyr Tyr Ala Gly
    50                  55                  60

Ala Asp Val Leu Arg Thr Glu Gln Asp Phe Tyr Asp Leu Thr Trp Ala
65                  70                  75                  80

Tyr Leu Gln Lys Cys Lys Ala Gln Asn Val Val His Val Glu Pro Phe
                85                  90                  95

Phe Asp Pro Gln Thr His Thr Asp Arg Gly Ile Pro Phe Glu Val Val
            100                 105                 110

Leu Ala Gly Ile Arg Ala Ala Leu Arg Asp Gly Glu Lys Leu Leu Gly
        115                 120                 125

Ile Arg His Gly Leu Ile Leu Ser Phe Leu Arg His Val Phe Asp Asp
    130                 135                 140

Met Ser Gln His Thr Ile Leu Asp Met Leu Glu Arg Gly Val Lys Val
145                 150                 155                 160

Thr Val Asn Ser Asp Asp Pro Ala Tyr Phe Gly Gly Tyr Val Thr Glu
                165                 170                 175

Asn Phe His Ala Leu Gln Gln Ser Leu Gly Met Thr Glu Glu
            180                 185                 190

<210> SEQ ID NO 9
<211> LENGTH: 95
<212> TYPE: PRT
<213> ORGANISM: Pseudomonas aeruginosa

<400> SEQUENCE: 9

Lys Ser Asp Lys Trp Ile Arg Arg Met Ala Gln Glu His Gly Met Ile
1               5                   10                  15

Glu Pro Phe Val Glu Arg Gln Val Arg Gly Ala Asp Asp Ser Arg Val
            20                  25                  30

Ile Ser Tyr Gly Val Ser Ser Tyr Gly Tyr Asp Val Arg Cys Ala Ala
        35                  40                  45
```

| | | | | | | | | | | | | |
|---|---|---|---|---|---|---|---|---|---|---|---|---|
| Glu | Phe | Lys | Val | Phe | Thr | Asn | Ile | His | Ser | Ala | Val | Val | Asp | Pro | Lys |
| | 50 | | | | | 55 | | | | | 60 | | | | |
| Asn | Phe | Asp | Glu | Lys | Ser | Phe | Val | Asp | Ile | Asn | Ser | Tyr | Lys | Asp | Arg |
| 65 | | | | | 70 | | | | | 75 | | | | | 80 |
| Gly | Gly | Lys | Tyr | Gln | Gly | Gln | Arg | Gly | Val | Thr | Leu | Pro | Lys | Ala | |
| | | | | 85 | | | | | 90 | | | | | 95 | |